United States Patent
Osmulski et al.

(10) Patent No.: US 11,020,383 B2
(45) Date of Patent: Jun. 1, 2021

(54) METHODS FOR THE TREATMENT OF CANCER METASTASIS

(71) Applicant: THE BOARD OF REGENTS OF THE UNIVERSITY OF TEXAS SYSTEM, Austin, TX (US)

(72) Inventors: Pawel A. Osmulski, San Antonio, TX (US); Maria E. Gaczynska, San Antonio, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 39 days.

(21) Appl. No.: 16/606,250

(22) PCT Filed: Apr. 19, 2018

(86) PCT No.: PCT/US2018/028283
§ 371 (c)(1),
(2) Date: Oct. 18, 2019

(87) PCT Pub. No.: WO2018/195263
PCT Pub. Date: Oct. 25, 2018

(65) Prior Publication Data
US 2020/0121661 A1    Apr. 23, 2020

Related U.S. Application Data

(60) Provisional application No. 62/487,600, filed on Apr. 20, 2017.

(51) Int. Cl.
| | | |
|---|---|---|
| *A61K 31/445* | (2006.01) | |
| *A61P 35/04* | (2006.01) | |
| *A61K 31/407* | (2006.01) | |
| *A61K 31/454* | (2006.01) | |
| *A61K 38/05* | (2006.01) | |
| *A61K 38/06* | (2006.01) | |
| *A61K 38/07* | (2006.01) | |
| *A61K 45/06* | (2006.01) | |
| *A61K 38/10* | (2006.01) | |

(52) U.S. Cl.
CPC .......... *A61K 31/445* (2013.01); *A61K 31/407* (2013.01); *A61K 31/454* (2013.01); *A61K 38/06* (2013.01); *A61K 38/07* (2013.01); *A61K 38/105* (2013.01); *A61K 45/06* (2013.01); *A61P 35/04* (2018.01)

(58) Field of Classification Search
CPC ............................. A61K 31/445; A61P 35/04
See application file for complete search history.

(56) References Cited

U.S. PATENT DOCUMENTS

| | | |
|---|---|---|
| 5,620,971 A | 4/1997 | Armistead et al. |
| 6,187,784 B1 | 2/2001 | Steiner et al. |
| 6,335,348 B1 | 1/2002 | Ross et al. |
| 6,376,517 B1 | 4/2002 | Ross et al. |
| 7,056,935 B2 | 6/2006 | Steiner et al. |
| 7,265,150 B1 | 9/2007 | Ross et al. |
| 2014/0154689 A1 | 6/2014 | Huang et al. |
| 2016/0116477 A1 | 4/2016 | Hoffmann et al. |
| 2016/0152567 A1 | 6/2016 | Osmulski et al. |

FOREIGN PATENT DOCUMENTS

| | | |
|---|---|---|
| WO | WO 2016/185026 | 11/1916 |
| WO | WO 2002/096420 | 12/2002 |
| WO | WO 2009/062881 | 5/2009 |
| WO | WO 2012/075048 | 6/2012 |
| WO | WO 2013/057281 | 4/2013 |
| WO | WO 2013/091900 | 6/2013 |

OTHER PUBLICATIONS

Adams et al., "Circulating giant macrophages as a potential biomarker of solid tumors," *Proc. Natl. Acad. Sci USA*, 111(9):3514-3519, 2014.
Chen et al., "Single-cell analysis of circulating tumor cells identifies cumulative expression patterns of EMT-related genes in metastatic prostate cancer," *Prostate*, 73(8):813-826, 2013.
Extended European Search Report issued in European Patent Application No. 14811064.6, 2017, dated Jan. 2, 2017.
Gast et al., "Cell fusion potentiates tumor heterogeneity and reveals circulating hybrid cells that correlate with stage and survival," *Sci. Adv.*, 4(9):eaat7828, 2018.
Giletto et al., "Pipecolic Esters as Minimized Templates for Proteasome Inhibition," *Org. Biomol. Chemistry*, 17:2734-2746, 2019.
Gopalakrishnan et al., "Evaluation of synthetic FK506 analogues as ligands for the FK506-binding proteins 51 and 52," *Journal of Medicinal Chemistry*, 55(9):4114-4122, 2012.
Hamilton et al., "Immunophilins: beyond immunosuppression," *Journal of Medicinal Chemistry*, 41(26):5119-5143, 1998.
Hamilton et al., "Synthesis of N-glyoxyl prolyl and pipecolyl amides and thioesters and evaluation of their in vitro and in vivo nerve regenerative effects," *Journal of Medicinal Chemistry*, 45(16):3549-3557, 2002.
Holt et al., "Design, synthesis, and kinetic evaluation of high-affinity FKBP ligands and the x-ray crystal structures of their complexes with FKBP12," *Chemical Society*, 115(22):9925-9938, 1993.
Huang et al., "TGF-β Signal Rewiring Sustains Epithelial-Mesenchymal Transition of Circulating Tumor Cells in Prostate Cancer Xenograft Hosts," *Oncotarget*, 7(47):77124-77137, 2016.
Joosse et al., "Biology, detection, and clinical implications of circulating tumor cells," *EMBO Mol Med*, 7(1):1-11, 2015.
Lander et al., "Complete subunit architecture of the proteasome regulatory particle," *Nature*, 482:186-191, 2012.

(Continued)

*Primary Examiner* — Noble E Jarrell
(74) *Attorney, Agent, or Firm* — Parker Highlander PLLC

(57) ABSTRACT

Provided herein are methods of preventing or treating cancer metastasis by administering an allosteric ligand of proteasomes. Further provided are methods of monitoring the efficacy of treatment with an allosteric ligand for reducing metastatic potential of a tumor.

22 Claims, 19 Drawing Sheets

(56) References Cited

OTHER PUBLICATIONS

Leach et al., "Fragment screening: An introduction," *Molecular Biosystems*, 2(9):429-446, 2006.

Liang et al., "Refined structure of the FKBP12-rapamycin-FRB ternary complex at 2.2 A resolution," *Acta Crystallographica Section D: Biological Crystallography*, 55(Pt. 4):736-44, 1999.

Lisi et al. "The MTOR Kinase Inhibitors Polarize Glioma-Activated Microglia to Express a M1 Phenotype" *Journal of Neuroinflammation*, vol. 11,125, pp. 1-10, 2014.

Ma and Blenis, "Molecular mechanisms of mTOR-mediated translational control," *Nature Reviews in Molecular and Cell Biology*, 10:307-318, 2009.

Massagué et al., "Metastatic colonization," *Nature*, 529(7586):298-306, 2016.

Osmulski and Gaczynska, "Rapamycin allosterically inhibits the proteasome," *Molecular Pharmacology*, 84:104-113, 2013.

Osmulski et al "Nanomechanical Biomarkers of Single Circulating Tumor Cells for Detection of Castration Resistant Prostate Cancer" *Prostate*, 74(13):1297-1307, 2014.

Osmulski et al., "A tetrahedral transition state at the active sites of the 20S proteasome is coupled to opening of the alpha-ring channel," *Structure*, 17(18):1137-47, 2009.

PCT International Search Report and Written Opinion issued in International Application No. PCT/US2018/028283, dated Jul. 5, 2018.

PCT International Search Report and Written Opinion issued in International Application No. PCT/US2014/042383, dated Sep. 30, 2014.

Soave et al., "The Fate of the Tumor in the Hands of Microenvironment: Role of TAMs and mTOR Pathway," *Mediators of Inflammation*, vol. 2016, Article ID 8910520, 7 pages Retrieved from the internet; URL: <http:/dx.doi.org/10.1155/2016/8910520>, 2016.

Wynn et al., "Origins and Hallmarks of Macrophages: Development, Homeostasis, and Disease," *Nature*, 496 (7446):445-55, 2013.

EpCAM - epithelial cell adhesion molecule; marker for typical CTCs

Vimentin - marker of EMT

EpCAM - epithelial cell adhesion molecule; marker for typical CTCs
CD11c$^+$ CD14$^{+/-}$ - M2 type macrophages in mice (anti-inflammatory; "chaperones")
CD14$^+$ CD11C$^-$ - M1 type macrophages in mice (pro-inflammatory; "predators" of CTCs)

METHODS FOR THE TREATMENT OF CANCER METASTASIS

This application is a national phase application under 35 U.S.C. § 371 of International Application No. PCT/US2018/028283, filed Apr. 19, 2018, which claims benefit of priority to U.S. Provisional Application Ser. No. 62/487,600, filed Apr. 20, 2017, the entirety of each of which is incorporated herein by reference.

A. FIELD OF THE DISCLOSURE

The present disclosure relates generally to the fields of biology and medicine. More particularly, it concerns methods for the prevention and treatment of cancer metastasis.

B. DESCRIPTION OF RELATED ART

Metastasis is the main cause of death in people with cancer. To colonize distant organs, circulating tumor cells must overcome many obstacles through mechanisms including infiltrating distant tissue, evading immune defenses, adapting to supportive niches, surviving as latent tumor-initiating seeds and eventually breaking out to replace the host tissue (Massague et al., 2016). These mechanisms make metastasis a highly inefficient process. However, once metastases have been established, current treatments frequently fail to provide durable responses. An improved understanding of the mechanistic determinants of such colonization is needed to better prevent and treat metastatic cancer. Although there are good means to delay or stop the growth of primary tumor sites, options to halt metastasis are very limited. Anti-metastatic drug options are extremely limited and often highly toxic.

Current methods usually target primary sites to restrain further growth and the dissemination of circulating tumor cells (CTCs). CTCs are shed from primary tumors of epithelial origin to the bloodstream. Most CTCs die in circulation, however, some that survive undergo epithelial-to-mesenchymal transition (EMT) and seed metastatic sites. CTCs can be isolated from the blood of cancer patients or animal cancer models by several methods, such as size-exclusion (i.e., microfiltration).

Studies with CTCs isolated from the blood of human prostate cancer patients and of mouse models of prostate cancer revealed that CTCs are accompanied by large cells of immune origin identified by their size and surface markers as macrophages (Huang et al., 2016). Indeed, there are sizable populations of tumor-associated macrophages (TAMs) inhabiting solid tumors which are hijacked by the tumor to protect it.

Circulating macrophages are known to appear in large numbers in inflammatory diseases, and they may exhibit pro-inflammatory or anti-inflammatory properties, depending on their type of activation. Tumor protecting TAMs are of the anti-inflammatory (M2) type. Conversely, pro-inflammatory macrophages (M1) phagocytize tumor cells. While it is known that M2 macrophages play the role of chaperones protecting CTCs from the physical strains of blood stream, there is an unmet need for methods to target CTCs and associated macrophages for the prevention and treatment of cancer metastasis.

SUMMARY

Thus, embodiments of the present disclosure concern methods of preventing or treating cancer metastasis as well as methods of monitoring the effectiveness of a therapy at decreasing the metastatic potential of a cancer.

In one embodiment, the present disclosure provides a method of preventing or treating cancer metastasis in a subject comprising administering to the subject an effective amount of B1, wherein administering B1 results in a decreased ratio of M2 macrophages to M1 macrophages in said subject.

In some aspects, the ratio of M2 macrophages to M1 macrophages is decreased at least 2-fold as compared to the ratio prior to administering B1. In certain aspects, the ratio of M2 macrophages to M1 macrophages is decreased at least 2.5, 3, 3.5, or 4-fold as compared to the ratio prior to administering B1. In some aspects, the ratio of M2 macrophages to M1 macrophages is decreased at least 4.5, 5, 6, 7, 8, 9, or 10-fold as compared to the ratio prior to administering B1. In particular aspects, the ratio of M2 macrophages to M1 macrophages is measured from pre-treatment and post-treatment blood samples obtained from said subject. In some aspects, said subject has been determined to have a M2 macrophage to M1 macrophage ratio greater than 1 prior to administering B1. In specific aspects, said subject has been determined to have a M2 macrophage to M1 macrophage ratio greater than 2, such as 2.1, 2.2, 2.3, 2.4, 2.5, 2.7, 2.8, 2.9, 3.0, 3.1, 3.2, 3.3, 3.4, 3.5, 4, or 5, prior to administering B1.

In certain aspects, preventing or treating cancer metastasis is further defined as reducing the metastatic potential of a cancer by interfering with the interaction of circulating tumor cells (CTCs) and tumor-associated macrophages (TAMs) in said subject, and/or decreased CTC aggressiveness in said subject. In specific aspects, preventing or treating cancer metastasis results in decreased CTCs and TAMs. In some aspects, said subject has been determined to have an increased number of CTCs and/or TAMs in the pre-treatment sample as compared to a control level. In specific aspects, the CTCs express EpCAM and/or an EMT marker. In particular aspects, the EMT marker is selected from the group consisting of vimentin, N-cadherin, FSP1, β-catenin, Snail, Slug, ZEB1, and α-SMA. In one specific aspects, the EMT marker is vimentin.

In some aspects, the cancer is lung, breast, brain, ovary, head and neck, liver, pancreas, or prostate cancer. In particular aspects, the cancer is prostate cancer. In one specific aspects, the prostate cancer is androgen-independent prostate cancer.

In certain aspects, B1 is administered to the patient once. In some aspects, B1 is administered to the patient two or more times, such as 3, 4, or 5 times. In particular aspects, B1 is administered intravenously.

In certain aspects, the activity of M2 macrophages in said subject is reduced, and/or the activity of M1 macrophages in said subject is not affected. In certain aspects, treating has no effect on the size or growth rate of a primary tumor.

In additional aspects, the method further comprises a second therapy. The second therapy may be one or more therapeutic agents, a surgery, a radiotherapy, or an immunotherapy, such as low dose radiotherapy or low dose immunotherapy. The second therapy may be is a chemotherapeutic agent, such as a low dose of said chemotherapeutic agent.

The chemotherapeutic agent may be a proteasome inhibitor, such as bortezomib, carfilzomib, ixazomib, delanzomib, oprozomib, or marizomib.

In a further embodiment, the present disclosure provides a method of evaluating the efficacy of a compound in reducing metastatic potential of a cancer cell comprising determining the ratio of M2 macrophages to M1 macrophages in a post-treatment sample. In some aspects, the compound is an allosteric ligand of proteasomes. In particular aspects, the allosteric ligand of proteasomes is B1, B2, B3, B4, or B5. In specific aspects, the allosteric ligand of proteasomes is B1.

In some aspects, the method further comprises determining the ratio of M2 macrophages to M1 macrophages in a pre-treatment sample. In particular aspects, the pre-treatment and post-treatment samples are blood samples.

In certain aspects, a M2 macrophage to M1 macrophage ratio between 0.1 and 1 (e.g., 0.2, 0.3, 0.4, 0.5, 0.6, 0.7, 0.8, or 0.9) indicates efficacy of the compound. In particular aspects, a M2 macrophage to M1 macrophage ratio greater than 1 (e.g., 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 3.0, 4, or 5) indicates a lack of efficacy of the compound. In some aspects, a M2 macrophage to M1 macrophage ratio of the post-treatment sample essentially equal to or increased as compared to the M2 macrophage to M1 macrophage ratio of the pre-treatment sample indicates a lack of efficacy of the compound. In other aspects, a M2 macrophage to M1 macrophage ratio of the post-treatment sample is decreased as compared to the M2 macrophage to M1 macrophage ratio of the pre-treatment sample indicates efficacy of the compound. In some aspects, the decrease is at least 2-fold (e.g., 2.5 or 3-fold). In further aspects, the decrease is at least 4-fold. In particular aspects, the decrease is at least 5-fold.

In additional aspects, the method further comprises characterizing the CTCs in said pre-treatment and/or post-treatment sample. In some aspects, characterizing comprises quantifying the number of CTCs. In particular aspects, quantifying the number of CTCs comprises counting the number of cells positive for EpCAM and/or an EMT marker in said sample. In some aspects, the EMT marker is selected from the group consisting of vimentin, N-cadherin, FSP1, β-catenin, Snail, Slug, ZEB1, and α-SMA. In one specific aspect, the EMT marker is vimentin. In some aspects, a decrease in the quantity of CTCs in the post-treatment sample as compared to the pre-treatment sample indicates efficacy of the compound. In particular aspects, the decrease is at least 2-fold (e.g., 2.5 or 3-fold). In some aspects, the decrease is at least 4-fold (e.g., 4.5, 5, 6, 7, 8, 9, or 10-fold). In other aspects, essentially no change or an increase in the quantity of CTCs indicates a lack of efficacy of the compound. In particular aspects, characterizing comprises determining the aggressiveness of CTCs in said pre-treatment and/or post-treatment sample by performing biophysical profiling. In particular aspects, decreased aggressiveness of CTCs in the post-treatment sample as compared to CTCs in the pre-treatment sample indicate efficacy of the compound. In some aspects, decreased aggressiveness is further defined as a higher Young modulus, decreased deformation, and/or decreased adhesion. In certain aspects, decreased aggressiveness is further defined as a higher Young modulus. In some aspects, decreased aggressiveness is further defined as decreased deformation. In certain aspects, decreased aggressiveness is further defined as decreased adhesion.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 17A) Human cultured monocytic U937 cells were in vitro differentiated into M0 macrophages and then polarized into M1-type and M2-type macrophages, in the presence of vehicle (DMSO; control) or in the presence of 1 µM B1. The inventors used established protocol to differentiate U937 cells into macrophages (M0) with PMA (phorbol myristate acetate) and then polarize them into model M1 and M2-like types with interferon γ and LPS (lipopolysaccharide) or interleukins IL-4 and IL-13, respectively. The identity of M1-type and M2-type model macrophages was confirmed by cell staining with specific markers: the fluorescent antibodies recognizing surface proteins CD80 (for M1) and CD163 (for M2). (FIG. 17B) Counts of live cells cultured in the presence or absence of B1 are presented. The counts of M1 model macrophages did not differ between control and B1-treated groups (mean±SD; n=4). In the case of M2-type model macrophages, the difference was statistically significant (T test, n=4).

DESCRIPTION OF ILLUSTRATIVE EMBODIMENTS

Figure 1:
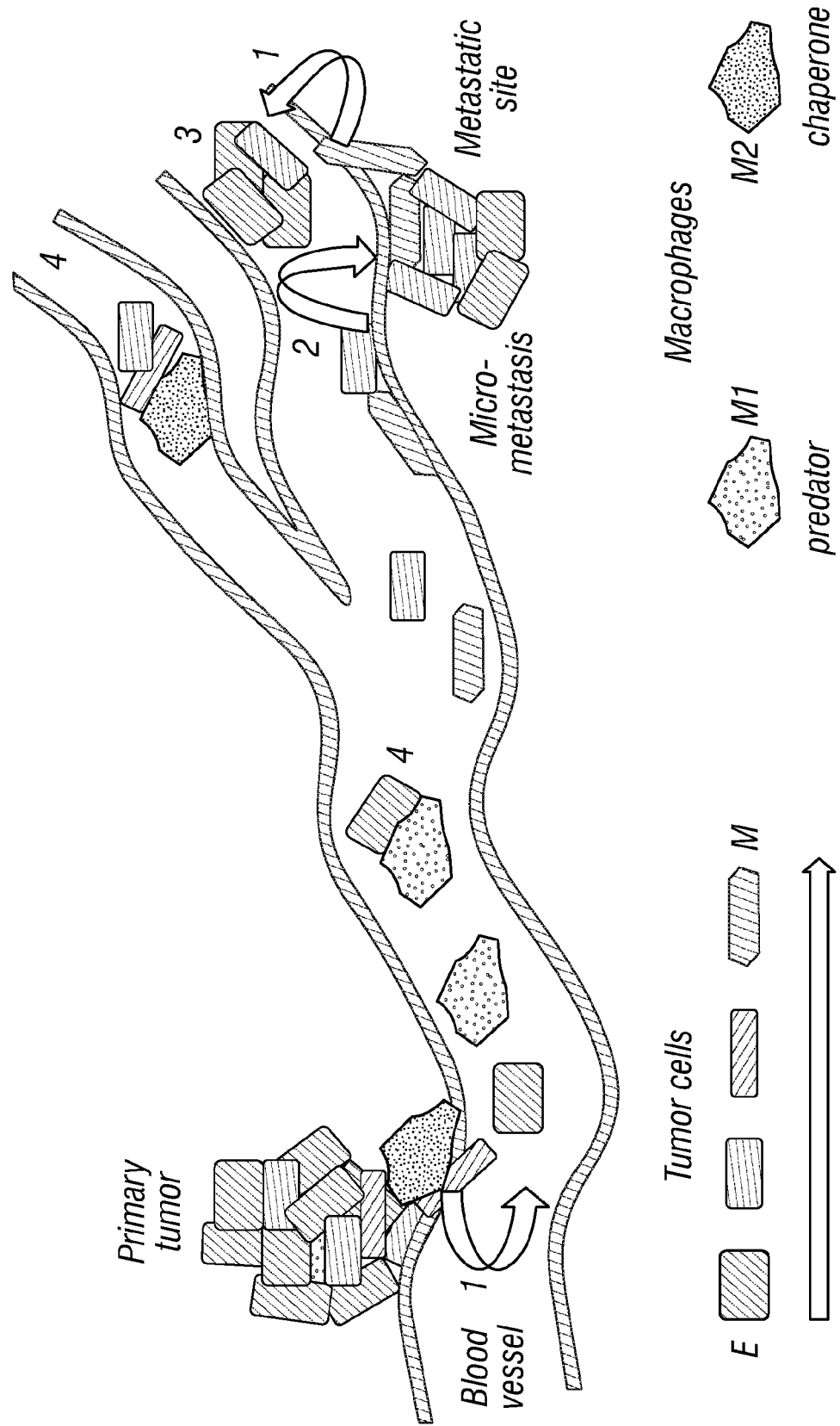
FIG. 1: Schematic depicting circulating tumor cells (CTCs) and associated immune cells in accord with studies on human prostate cancer patients and mouse cancer models.

The proteasome represents a broadly accepted target for ligands in the fight against cancer. The present disclosure relates to the use of allosteric ligands which act to inhibit proteasome activity. One exemplary allosteric ligand is the compound, B1, (3-(3,4,5-trimethoxyphenyl)propyl 1-(2-cyclohexyl-2-oxoacetyl) piperidine-2-carboxylate; disclosed in U.S. Patent Publication No. US20160152567, incorporated herein by reference in its entirety) which interferes with 26S assembling and influences proteasome activities at nanomolar concentrations while not affecting mTOR pathway. In addition, B1 increases affinity of core particle toward bortezomib leading to strong cytotoxic effects on cultured breast cancer cells, which are poorly responsive to bortezomib.

In the present studies, the administration of B1 in mouse models demonstrated not only a reduction in tumor size, but also a reduced number of circulating tumor cells (CTC) that are responsible for metastasis. Additionally, the number of chaperone macrophages thought to assist tumor cells in migrating to new sites was significantly reduced. Limiting the abundance of cells, particularly macrophages that help CTCs to survive in the blood stream and colonize metastatic sites is a unique, novel and unexpected property of the B1 compound. By limiting the dissemination of CTCs, the allosteric ligand of proteasomes can decrease or prevent metastasis.

Specifically, the influence of B1 on the abundance of CTCs, their mechanical properties and abundance of macrophages was confirmed in a mouse model of prostate cancer in the present studies. The experiments were performed with both nude and CB. 17 SCID mice. It was found that the treatment of mice with xenografted prostate tumors with Compound B1 decreases the abundance of cancer cells present in the blood stream by about five-fold compared to the control, vehicle only treated animals. Moreover, such cells showed decreased invasiveness based upon their mechanical properties. In addition, there was a decrease of about four-fold of chaperone immune cells (i.e., M2 macrophages, also referred to as tumor-associated macrophages (TAMs)). Surprisingly, treatment with B1 resulted in a decrease of the ratio of M2 macrophages to M1 macrophages by five-fold as compared to the ratio of M2:M1 in the vehicle-treated mouse. Accordingly, embodiments of the present disclosure concern the use of allosteric ligands of proteasomes, such as B1, to decrease or prevent cancer metastases, alone or combination with bortezomib.

In addition, the present disclosure provides methods of assessing drug effectiveness by determining the M2 macrophage ratio to M1 macrophage ratio and/or biophysical profiling of CTCs before and after administration of the drug, such as B1. As the present studies indicated, increased metastatic potential was observed to correlate with an increased M2:M1 ratio while treatment with B1 resulted in a decreased M2:M1 ratio. Thus, a measuring a decrease in the M2:M1 after treatment with a drug, such as B1, would indicate that the drug was effective at decreasing metastatic potential. The biophysical profiling may be performed to measure Young modulus (i.e., smoothness), deformation, and/or adhesion. For example, the biophysical profiling may be performed as described in U.S. Patent Publication No. US2014/0154689 (incorporated herein by reference in its entirety).

These and other aspects of the disclosure are described in detail below.

I. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "===" represents a single bond or a double bond. Thus, for example, the structure

includes the structures

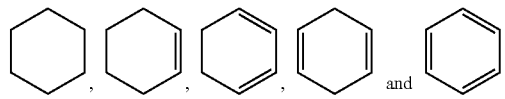

As will be understood by a person of skill in the art, no one such ring atom forms part of more than one double bond. The symbol " ~~ ", when drawn perpendicularly across a bond indicates a point of attachment of the group. It is noted that the point of attachment is typically only identified in this manner for larger groups in order to assist the reader in unambiguously identifying a point of attachment. The symbol "◤" means a single bond where the group attached to the thick end of the wedge is "out of the page." The symbol "◣" means a single bond where the group attached to the thick end of the wedge is "into the page". The symbol " ~~ " means a single bond where the conformation (e.g., either R or S) or the geometry is undefined (e.g., either E or Z). Similarly, the covalent bond symbol "—", when connecting stereogenic atom, does not indicate any preferred stereochemistry, it does cover all stereoisomers, including the "◤" and "◣" forms.

Any undefined valency on an atom of a structure shown in this application implicitly represents a hydrogen atom bonded to the atom. A bold dot on a carbon atom indicates that the hydrogen attached to that carbon is oriented out of the plane of the paper. When a group "R" is depicted as a "floating group" on a ring system, for example, in the formula:

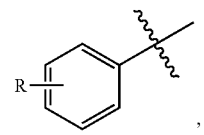

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

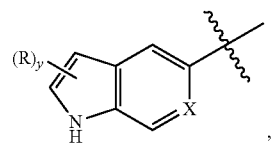

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene $_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

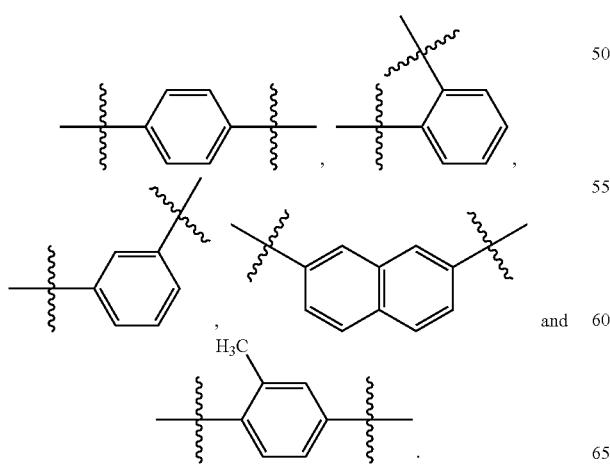

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "arene" refers to the compound H—R, wherein R is aryl. Benzene and toluene are non-limiting examples of arenes.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolinyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

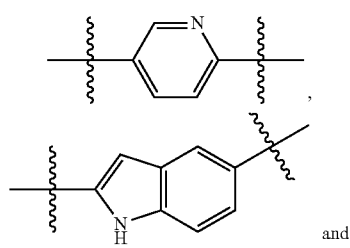

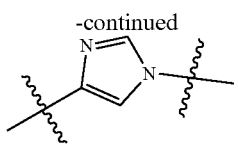

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. As used herein, the term does not preclude the presence of one or more double bonds in the ring or ring system, provided that the resulting groups remains non-aromatic. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When the term "heterocycloalkyl" used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —S(O)₂NH₂, or —C(O)OC(CH₃)₃ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃ (methoxy), —OCH₂CH₃ (ethoxy), —OCH₂CH₂CH₃, —OCH(CH₃)₂ (isopropoxy), —O(CH₃)₃ (tert-butoxy), —OCH(CH₂)₂, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The term "alcohol" corresponds to an alkane, as defined above, wherein at least one of the hydrogen atoms has been replaced with a hydroxy group. Similarly, the term "ether" corresponds to an alkane, as defined above, wherein at least one of the hydrogen atoms has been replaced with an alkoxy group.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups —NHC(O)OCH₃ and —NHC(O)NHCH₃ are non-limiting examples of substituted amido groups.

The terms "alkylsulfonyl" and "alkylsulfinyl" when used without the "substituted" modifier refers to the groups —S(O)₂R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which causes 50% inhibition of a given process. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer.

In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the phrase "metastatic cancer" or "cancer metastasis" is defined as cancers that have potential to spread to other areas of the body. Common metastasizing cancers include breast, lung, renal, multiple myeloma, thyroid and prostate. By way of example, other cancers that have the potential to metastasize include but are not limited to adenocarcinoma, blood "cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma and squamous cell cancer.

The term of "efficacy" of a treatment, such as compound B1, used herein is referred to as the effect of a treatment on the progression of tumors and/or metastatic potential of a tumor. The efficacy can be determined by the response rate of the patient concerned by said treatment. For example, after being treated by the treatment, if the tumor size of the patient decreased at least 20% from the initial size there of before treatment in 3 months, the patient is deemed as response to the treatment. The response rate can be calculated by the number of patients having response out of the total number of the patient monitored.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice methods of the present disclosure.

II. Allosteric Ligands of Proteasomes

Allosteric ligands of proteasomes, such as the compound B1, are disclosed in U.S. Patent Publication No. US20160152567, incorporated herein by reference in its entirety. In some embodiments, the compound is described by the formula:

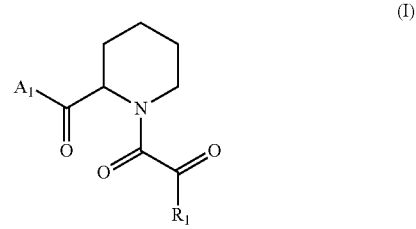

(I)

wherein: $A_1$ is hydroxy, amino, or

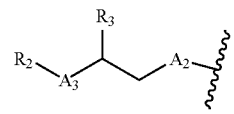

wherein: $A_2$ is —O— or —$NR_6$— wherein $R_6$ is hydrogen, alkyl$_{(C≤6)}$ or substituted alkyl$_{(C≤6)}$; $A_3$ is alkanediyl$_{(C≤6)}$, alkenediyl$_{(C≤6)}$, or a substituted version of either of these groups; $R_2$ is

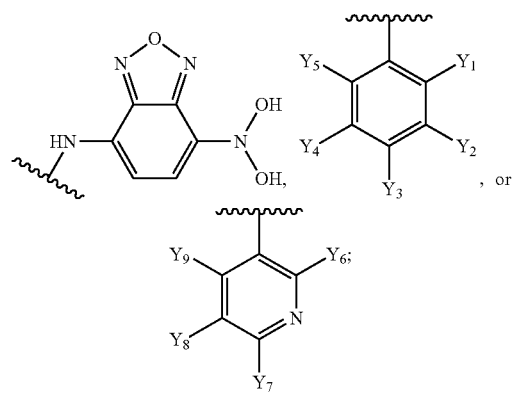

wherein: $Y_1$, $Y_2$, $Y_3$, $Y_4$, $Y_5$, $Y_6$, $Y_7$, $Y_8$, and $Y_9$ are each independently hydrogen, hydroxy, phosphate, halo, alkyl$_{(C≤12)}$, alkoxy$_{(C≤12)}$, acyloxy$_{(C≤12)}$, heteroaryl$_{(C≤12)}$, acyl$_{(C≤12)}$, alkylamino$_{(C≤12)}$, dialkylamino$_{(C≤12)}$, or a substituted version of any of these groups; $R_3$ is hydrogen, alkyl$_{(C≤8)}$, or a substituted alkyl$_{(C≤8)}$; and $R_1$

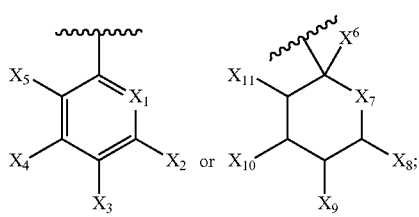

wherein: $X_1$ is O, N, or $CR_4$; $X_2$, $X_3$, $X_4$, $X_5$, and $R_4$ are each independently hydrogen, hydroxy, phosphate, halo, alkyl$_{(C\leq 12)}$, alkoxy$_{(C\leq 12)}$, acyloxy$_{(C\leq 12)}$, heteroaryl$_{(C\leq 12)}$, acyl$_{(C\leq 12)}$, alkylamino$_{(C\leq 12)}$, dialkylamino$_{(C\leq 12)}$, or a substituted version of any of these groups; $X_6$ is hydrogen or hydroxy; $X_7$ is O, NH, or $C(R_5)_2$; $X_8$, $X_9$, $X_{10}$, $X_{11}$, and $R_5$ are each independently hydrogen, hydroxy, phosphate, halo, alkyl$_{(C\leq 12)}$, alkoxy$_{(C\leq 12)}$, acyloxy$_{(C\leq 12)}$, heteroaryl$_{(C\leq 12)}$, acyl$_{(C\leq 12)}$, alkylamino$_{(C\leq 12)}$, dialkylamino$_{(C\leq 12)}$, or a substituted version of any of these groups; or a pharmaceutically acceptable salt thereof.

In some embodiments, the compounds that may act as allosteric ligands for proteasome include compounds of the formula:

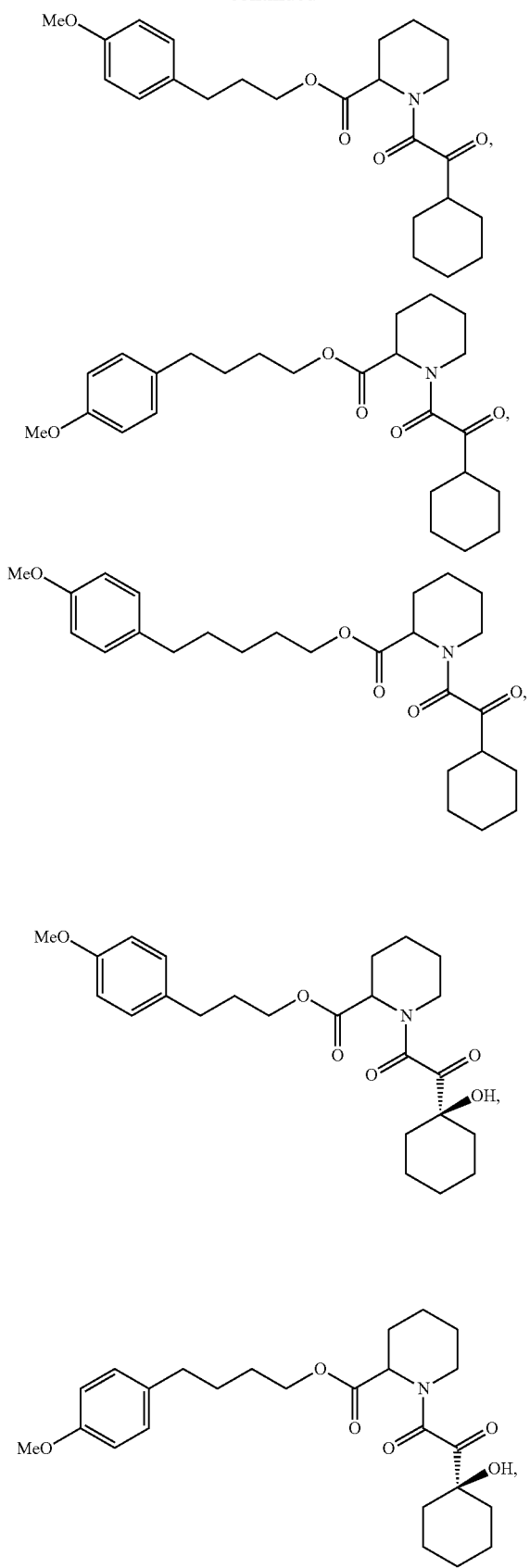

23
-continued
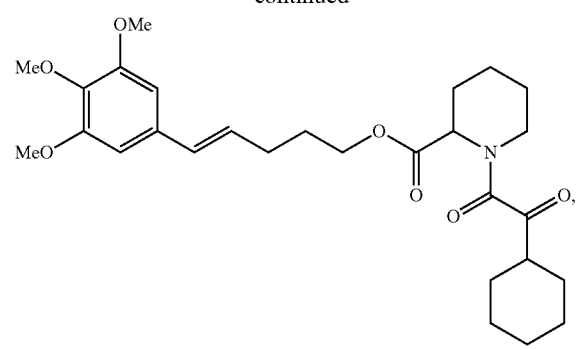
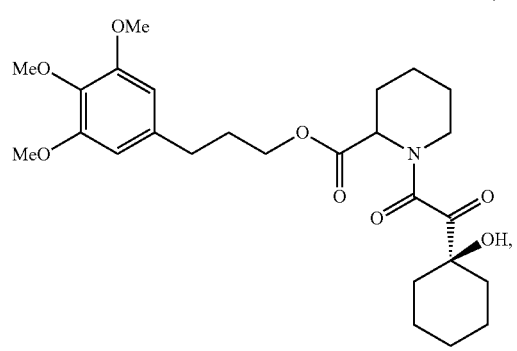
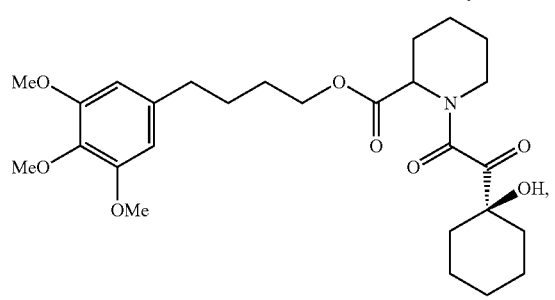
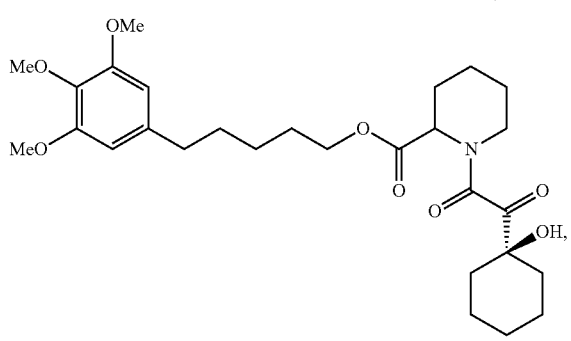
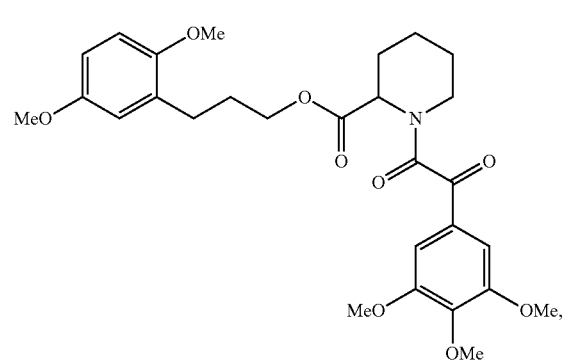
24
-continued
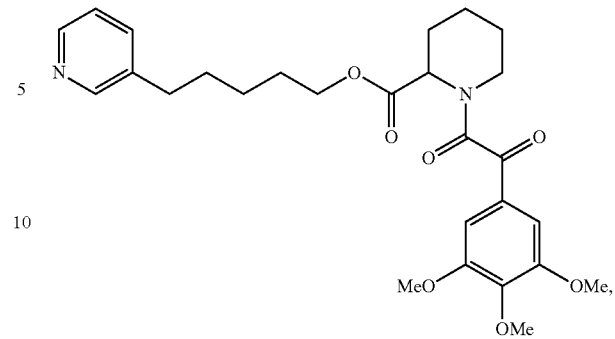
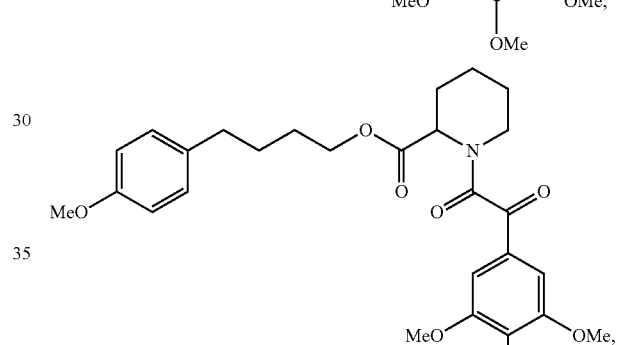
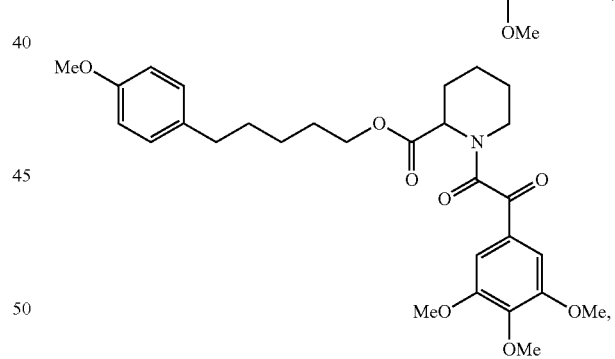

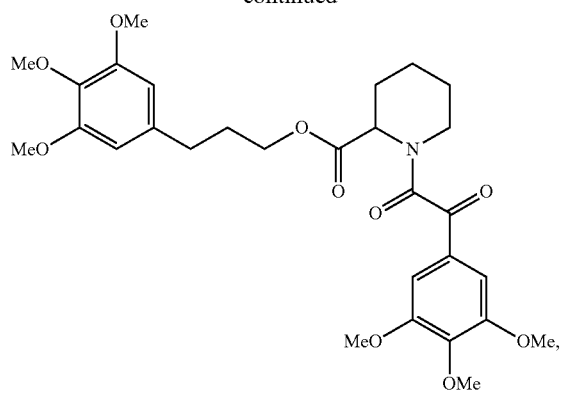

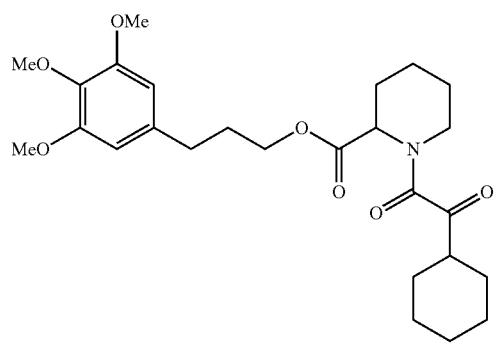 [SMILES: COc1cc(CCCOC(=O)C2CCCCN2C(=O)C(=O)C2CCCCC2)cc(OC)c1OC]

or a pharmaceutically acceptable salt thereof. In some embodiments, the compound has a formula:

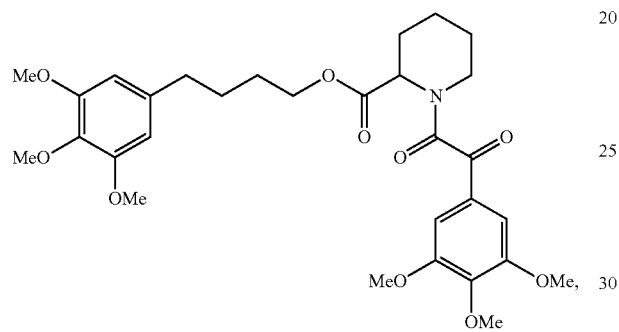

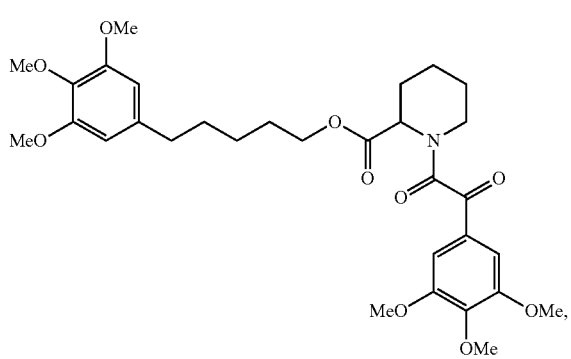

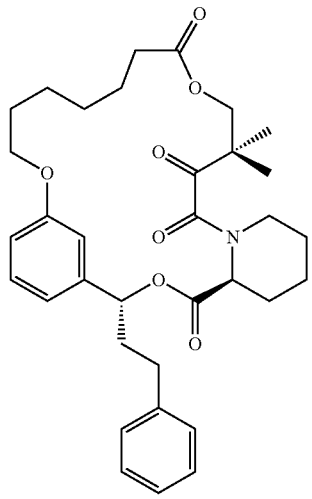

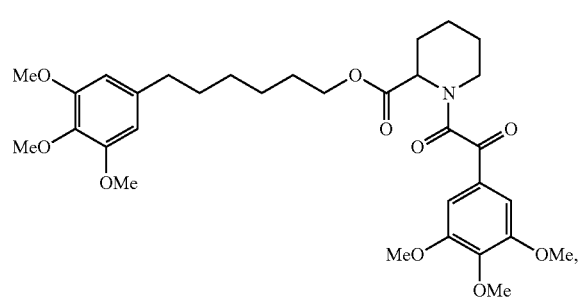

or a pharmaceutically acceptable salt thereof. In some embodiments, the compound is preferentially of the formula:

or a pharmaceutically acceptable salt thereof. The above described compounds are the preferred embodiment of the compounds of the disclosure and can be prepared as described in this application or through the methods described in the art without undue experimentation. In some aspects of the present disclosure, the compounds may also be referenced by their name, an abbreviation or other property. The following table provides appropriate names and abbreviations for some of the compounds described in the present disclosure.

TABLE 1

COMPOUNDS OF THE PRESENT DISCLOSURE

| Abbreviation | Compound |
| --- | --- |
| B0 | *(structure: piperidine-2-carboxylic acid N-acylated with cyclohexylglyoxylyl group)* |
| B1 | *(structure: piperidine-2-carboxylic acid 3-(3,4,5-trimethoxyphenyl)propyl ester, N-acylated with cyclohexylglyoxylyl group)* |
| B2 | *(structure: piperidine-2-carboxamide with N-[3-(3,4,5-trimethoxyphenyl)propyl], N-acylated with cyclohexylglyoxylyl group)* |
| B3 | *(structure: piperidine-2-carboxylic acid 2-{[7-(N,N-dihydroxyamino)benzo[1,2,5]oxadiazol-4-yl]amino}ethyl ester, N-acylated with cyclohexylglyoxylyl group)* |

TABLE 1-continued

COMPOUNDS OF THE PRESENT DISCLOSURE

| Abbreviation | Compound |
|---|---|
| B4 | [structure: piperidine-N-acylated with oxo-cyclohexylacetyl group; carboxylate ester linked via –O–CH₂CH₂CH₂–CH=CH– to 3,4,5-trimethoxyphenyl] |
| B5 | [structure: piperidine-N-acylated with oxo-cyclohexylacetyl group; carboxylate ester linked via –O–(CH₂)₄– to 3,4,5-trimethoxyphenyl] |

The allosteric ligands for proteasome used in the present disclosure can be prepared according to the methods described in US20160152567. The methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The allosteric ligands for proteasomes described in this disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The allosteric ligands for proteasome may occur as racemates and racemic mixtures, single enantiomers, diastereomeric mixtures and individual diastereomers. In some embodiments, a single diastereomer is obtained. The chiral centers of the present invention can have the S or the R configuration.

In addition, atoms making up the allosteric ligands of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of the novel allosteric ligands for proteasome may be replaced by a sulfur or selenium atom(s).

The allosteric ligands for proteasome may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical advantages over, compounds known in the prior art for use in the indications stated herein.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the present disclosure contemplates prodrugs of compounds of the present invention as well as methods of delivering prodrugs. Prodrugs of the compounds employed in the present disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

III. Cancer Metastasis

Although the genetic basis of tumorigenesis may vary between different cancer types, the cellular and molecular mechanisms required for metastasis seems to be similar for all the solid tumor types. During a metastatic cascade, the cancer cells lose growth inhibitory response, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. The molecular mechanisms that drive invasion and metastasis are similar to those found in embryonic development, trophoblast implantation, and mammary gland development.

Studies have found that in human prostate cancer patients and in mouse cancer models the enumeration of distinct types of macrophages could be used as a prognostic marker alongside CTC enumeration. Namely, a large number of anti-inflammatory circulating macrophages indicated a high metastatic potential and poor prognosis. It has also been shown that physical contacts between macrophages and CTCs help to pull CTCs across capillary walls in the lungs.

Macrophages, the most plastic cells of the hematopoietic system, are found in all tissues and show great functional diversity. They have roles in development, homeostasis, tissue repair and immunity (Wynn et al., 2013; incorporated herein by reference). Although tissue macrophages are anatomically distinct from one another, and have different transcriptional profiles and functional capabilities, they are all required for the maintenance of homeostasis. However, these reparative and homeostatic functions can be subverted by chronic insults, resulting in a causal association of macrophages with disease states. The 'hallmarks' of macrophages are defined according to the states that they adopt during the performance of their various roles, taking into account new insights into the diversity of their lineages, identities and regulation.

FIG. 1 presents the natural history of CTCs (circulating tumor cells) and associated immune cells, proposed in accord with studies on human prostate cancer patients and in mouse cancer models. In particular, the graph shows a scheme of a blood vessel with nearby primary tumor sites. When epithelial tumor cells from the primary site get into blood vessels (i.e., intravasate) they become CTCs that use the blood stream to reach distant sites in a patient body. If such site is receptive, CTCs can extravasate (i.e., leave the blood vessel) and establish metastatic sites. The pictured cells can be isolated from blood with the microfiltration method and are accessible for AFM studies, immunocytochemistry and single cell gene expression profiling. CTCs may intravasate as single cells or in clusters, the latter being much more invasive. CTCs undergo EMT enabling them to seed metastatic sites through extravasation. Metastatic sites can become additional sources of CTCs. Depending on the type of activation macrophages may play a role as cancer promoting chaperones of CTCs (M2) that help CTCs to travel through blood stream and reach the destination or, anti-tumor predators (M1) that capture and destroy CTCs. All of these cell types can be isolated as heterogeneous clusters or CTC-macrophage pairs.

In some aspects, the present disclosure concerns the detection of CTCs. To date, more than 40 techniques have been developed for CTC detection and novel strategies are published continuously (Joosse et al., 2015; incorporated herein by reference). Exemplary methods of CTC detection and isolation are described herein. CTC enrichment and detection methods have been classified based on whether they exploit the physical or biological properties of the cells. However, as many enrichment strategies rely on positive selection (usually targeting EpCAM), CTC assays are more commonly grouped into label-dependent and label-independent approaches. Among the numerous EpCAM-based CTC detection technologies, the semi-automated CellSearch® system is the most frequently used system and at present the only one cleared by the U.S. FDA. Through this approach, CTC counts have been associated with an independent prognostic power on progression-free survival (PFS) and overall survival (OS) in primary and metastatic disease. Due to its clinical relevance, high reproducibility, and FDA clearance, CellSearch® can be considered as a benchmark for all other CTC detection methods appearing on the market. The AdnaTest® is another epithelial marker-based research tool that positively enriches CTCs from a blood sample. Using this approach, the presence or disappearance of CTCs was shown to be a prognostic and predictive marker in a study on metastatic breast cancer. Microfluidic device platforms like the CTC- or the Herringbone (HB)-Chip seem to be promising alternatives to selectively capture EpCAM-positive CTCs in cancer patients. A combination of anti-EpCAM and anti-MUC 1 capture in a single microfluidic device may further result in an improved capture performance of CTCs. Another chip-based platform combines a size-based filtration with an affinity-based enrichment strategy, thus enhancing the chance of systematic removal of PBMCs and RBCs (CTC-iChip). Fluxion Biosciences has lately introduced a commercially available microfluidic technology (IsoFlux®) with magnetic isolation zones to isolate EpCAM-positive tumor cells from biological samples. Using the IsoFlux®, recovery rates between 74 and 85% of $EpCAM^{low}$-(MDA-MB-231) and $EpCAM^{high}$ (SKBR3)-expressing tumor cells could be obtained. To circumvent sample volume limitations, GILUPI GmbH has designed an EpCAM-coated wire (CellCollector™) to capture CTCs in vivo. This device is positioned through a cannula into the vein of a cancer patient. It is estimated that during the 30-min application time, up to 1.5 l of blood flows over the detector, thus increasing the yield of detectable CTCs.

IV. Methods of Use

While hyperproliferative diseases can be associated with any disease which causes a cell to begin to reproduce uncontrollably, the prototypical example is cancer. One of the key elements of cancer is that the cell's normal apoptotic cycle is interrupted and thus agents that lead to apoptosis of the cell are important therapeutic agents for treating these diseases. In this disclosure, the allosteric ligands have been shown to lead to decreased cell counts of CTCs and tumor associated macrophages and as such can potentially be used to treat a variety of types of cancers, particularly for the prevention or treatment of cancer metastasis. As such, the compounds described in the disclosure may be effective in treating cancers which form a solid tumor and have metastatic potential. In some embodiments, those cancers include metastatic breast cancer and prostate cancer. In other embodiments, the compounds described in the disclosure may be used to modulate the drug resistance of a solid tumor or a cancer of the blood. In various aspects, it is anticipated that the compounds of the present disclosure may be used to treat virtually any malignancy.

Methods of the present disclosure may results in the prevention, decrease, or inhibition of cancer metastasis, such as inhibiting the spread of tumor cells to distant organs. Thus, the disclosure provides methods of inhibiting, preventing, aiding in the prevention, or decreasing the symptoms associated with tumor/cancer metastasis.

In some embodiments of the methods for preventing or treating metastasis, a second agent is administered to the individual, such as an antineoplastic agent. In some embodiments, the second agent comprises a second metastasis-inhibiting agent, such as a CD26 antagonist, a plasminogen antagonist, or an adenosine deaminase antagonist. In other embodiments, the second agent is an angiogenesis inhibiting agent.

Cancer cells that may be treated with the compounds according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

In some embodiments of the methods for inhibiting or treating metastasis, the individual is afflicted with a hyperplastic condition, such as with cancer or with a tumor. The methods described herein are not limited to any particular hyperplastic condition. In specific embodiments, the individual is afflicted with at least one form of renal cell cancer, Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, testicular cancer, gastrointestinal cancer, or stomach cancer, or a combination thereof. In some embodiments, the individual is afflicted with one form of cancer that has metastasized to at least another tissue. For example, the individual may be afflicted with one form of breast cancer, such as basal like breast cancer, wherein breast cancer cells have metastasized to the liver or to the lungs.

The individual in need of the described treatment can be at risk for a metastatic condition, either genetically (e.g., through heredity) or environmentally, or the mammal can have one or more non-metastatic tumors. For example, the mammal can be at risk for or currently have one or more non-metastatic conditions selected from the group consisting of melanoma, breast cancer, ovarian cancer, prostate cancer, lung cancer, bone cancer, throat cancer, brain cancer, testicular cancer, liver cancer, stomach cancer, pancreatic cancer, and combinations thereof. Thus, the described treatment can be administered prophylactically or therapeutically. The described treatment can also be administered to a mammal having a metastatic condition to inhibit further metastasis.

A. Pharmaceutical Formulations and Routes of Administration

For administration to a mammal in need of such treatment, the allosteric ligands for proteasome in a therapeutically effective amount are ordinarily combined with one or more excipients appropriate to the indicated route of administration. The allosteric ligands for proteasome may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the allosteric ligands may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present disclosure may be subjected to conventional pharmaceutical operations such as sterilization and/or may contain conventional pharmaceutical carriers and excipients such as preservatives, stabilizers, wetting agents, emulsifiers, buffers, etc.

The allosteric ligands for proteasome may be administered by a variety of methods, e.g., orally or by injection (e.g. subcutaneous, intravenous, intraperitoneal, etc.). Depending on the route of administration, the novel allosteric ligands may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the allosteric ligands for proteasome with, or co-administer the novel allosteric ligands for proteasome with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The allosteric ligands for proteasome may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion are also envisioned. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the allosteric ligands for proteasome in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The allosteric ligands for proteasome can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the allosteric ligands may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the allosteric ligands for proteasome in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of the novel allosteric ligands for proteasome calculated to produce the desired therapeutic effect in association with the required pharmaceutical carrier. The specification for the dosage unit forms of the invention are dictated by and directly dependent on (a) the unique characteristics of the allosteric ligands for proteasome described in this invention and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The allosteric ligands for proteasome describe in this disclosure are administered at a therapeutically effective dosage sufficient to treat a condition associated with a condition in a patient. For example, the efficacy of the allosteric ligands for proteasome can be evaluated in an animal model system that may be predictive of efficacy in treating the disease in humans, such as the model systems shown in the examples and drawings.

The actual dosage amount of the allosteric ligands for proteasome of the present disclosure or composition comprising the inhibitors of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 1 mg/kg to about 50 mg/kg, in one or more dose administrations daily, for one or several days (depending of course of the mode of administration and the factors discussed above). In some particular embodiments, the amount is less than 5,000 mg per day with a range of 10 mg to 4500 mg per day.

The effective amount may be less than 10 mg/kg/day, less than 50 mg/kg/day, less than 100 mg/kg/day, less than 250 mg/kg/day. It may alternatively be in the range of 1 mg/kg/day to 250 mg/kg/day.

In other non-limiting examples, a dose may also comprise from about 0.1 mg/kg/body weight, about 1 mg/kg/body weight, about 10 g/kg/body weight, about 50 g/kg/body weight, or more per administration, and any range derivable therein. In non-limiting examples of a derivable range from the numbers listed herein, a range of about 1 mg/kg/body weight to about 50 mg/kg/body weight, about 5 g/kg/body weight to about 10 g/kg/body weight, etc., can be administered, based on the numbers described above.

In certain embodiments, a pharmaceutical composition of the present disclosure may comprise, for example, at least about 0.1% of an inhibitor described in the present disclosure. In other embodiments, the compound of the present disclosure may comprise between about 0.25% to about 75% of the weight of the unit, or between about 25% to about 60%, or between about 1% to about 10%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The allosteric ligands may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat. In some embodiments, the allosteric ligands of proteasome are taken before the onset of the tumor as a prophylaxis measure. In other embodiments, the allosteric ligands of proteasome are taken as a treatment option for use as an antiproliferative agent.

B. Combination Therapy

In addition to being used as a monotherapy, the allosteric ligands of proteasomes described in the present disclosure may also find use in combination therapies for the present methods of preventing or treating cancer metastasis. Effective combination therapy may be achieved with a single composition or pharmacological formulation that includes both agents, or with two distinct compositions or formulations, administered at the same time, wherein one composition includes an allosteric ligand of proteasome, and the other includes the second agent(s). The other therapeutic modality may be administered before, concurrently with, or following administration of the allosteric ligands of proteasome. The therapy using the allosteric ligands of proteasome may precede or follow administration of the other agent(s) by intervals ranging from minutes to weeks. In embodiments where the other agent and the compounds of the present disclosure which act as allosteric ligands of proteasome are administered separately, one would generally ensure that a significant period of time did not expire between each delivery, such that each agent would still be able to exert an advantageously combined effect. In such instances, it is contemplated that one would typically administer the allosteric ligands of proteasome and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of a novel allosteric ligand of proteasome, or the other agent will be desired. In this regard, various combinations may be employed. By way of illustration, where the novel allosteric ligand of proteasomes is "A" and the other agent is "B", the following permutations based on 3 and 4 total administrations are exemplary:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated. Non-limiting examples of pharmacological agents that may be used in the present invention include any pharmacological agent known to be of benefit in the treatment of a cancer or hyperproliferative disorder or disease. In some embodiments, combinations of the allosteric ligands of proteasome with a cancer targeting immunotherapy, radiotherapy, chemotherapy, or surgery are contemplated.

Also contemplated is a combination of the allosteric ligands of proteasome with more than one of the above mentioned methods including more than one type of a specific therapy. In some embodiments, the compounds of the present invention are given in conjunction with the chemotherapeutic agent, bortezomib. In some embodiments, the compounds of the present invention are given in conjunction with the chemotherapeutic agent, PR-171. In some embodiments, it is contemplated that the immunotherapy is a monoclonal antibody which targets HER2/neu such trastuzumab (Herceptin®), alemtuzumab (Campath®), bevacizumab (Avastin®), cetuximab (Erbitux®), and panitumumab (Vectibix®) or conjugated antibodies such as ibritumomab tiuxetan (Zevalin®), tositumomab (Bexxar®), brentuximab vedotin (Adcetris®), ado-trastuzumab emtansine (Kadcyla™), or denileukin dititox (Ontak®) as well as immune cell targeting antibodies such as ipilimumab (Yervoy®), tremelimumab, anti-PD-1, anti-4-1-BB, anti- GITR, anti-TIM3, anti-LAG-3, anti-TIGIT, anti-CTLA-4, or anti-LIGHT. Furthermore, in some embodiments, the allosteric ligands of proteasome are envisioned to be used in combination therapies with dendritic cell-based immunotherapies such as Sipuleucel-T (Provenge®) or adoptive T-cell immunotherapies.

Furthermore, it is contemplated that the allosteric ligands of proteasome are used in combination with a chemotherapeutic agent such as PR-171 (Kyprolis®), bortezomib (Velcade®), anthracyclines, taxanes, methotrexate, mitoxantrone, estramustine, doxorubicin, etoposide, vinblastine, carboplatin, vinorelbine, 5-fluorouracil, cisplatin, topotecan, ifosfamide, cyclophosphamide, epirubicin, gemcitabine, vinorelbine, irinotecan, etoposide, vinblastine, pemetrexed, melphalan, capecitabine, oxaliplatin, BRAF inhibitors, and TGF-beta inhibitors. In some embodiments, the combination therapy is designed to target a cancer such as those listed above. In the preferred embodiments, the cancer the combination therapy is designed to treat is breast cancer or another solid tumor. In other embodiments, the cancer combination therapy is used to treat blood cancers by modulating their drug resistance.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gamma1I and calicheamicin omega1I); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells.

CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

V. Examples

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Administration of B1 Results in Decreased CTCs and Macrophages

Figure 2:
FIG. 2: Growth of primary tumor in nude mice xenografted with human prostate cancer androgen resistant CD-2 cells treated with vehicle or B1 up to 35 days post injection.
Figure 2:
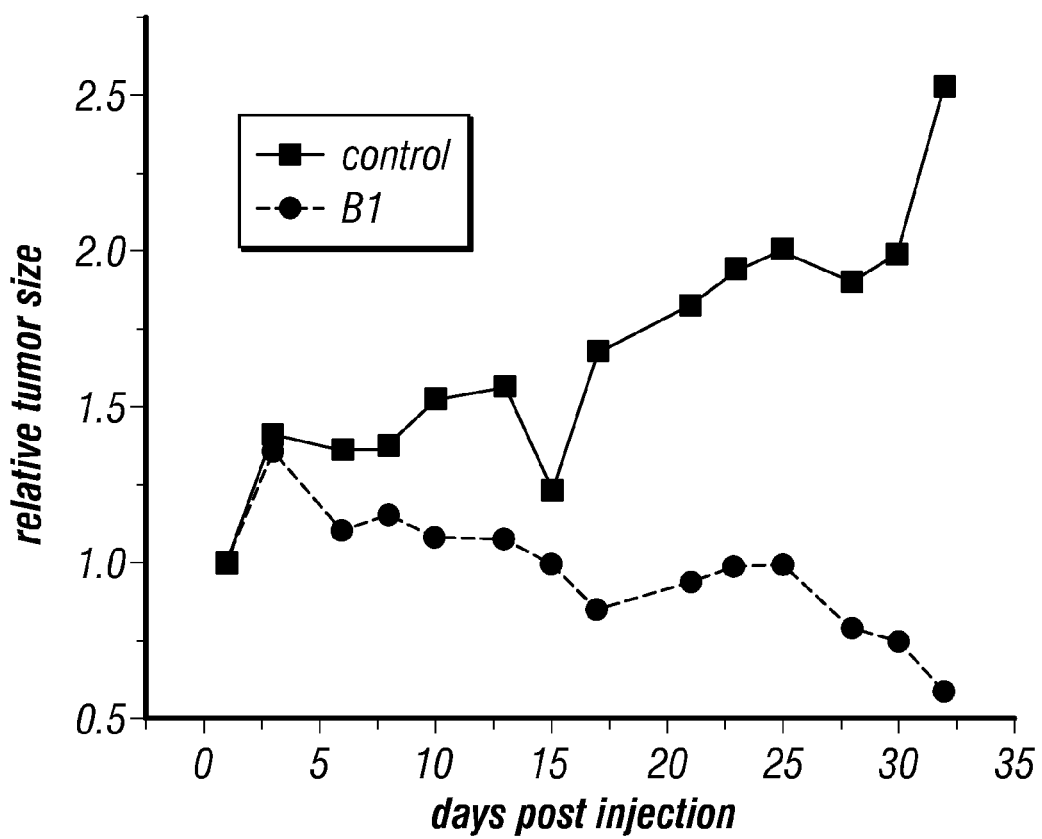

CTCs and macrophages were isolated from the blood of two nude mice xenografted with human prostate cancer androgen resistant C4-2 cells and treated biweekly intratumorally with vehicle or B1 (30 mg/kg). In the vehicle-treated mouse, the tumor grew by size more than twice in the span of four weeks, whereas in the B1-treated mouse the tumor shrunk to about 50% of the size at the start of treatment (FIG. 2).

The anti-tumor actions of B1 in nude mice were confirmed by analysis of circulating tumor cells (CTCs). Enumeration of CTCs is used as a prognostic marker in cancer patients. The enumeration was extended to include not only canonical CTCs positive for epithelial marker EpCAM, but also EpCAM negative CTC-like cells positive for markers of epithelial-mesenchymal transition (EMT), indicative of increased aggressiveness of the cells (Chen et al., 2013).

Figure 3:
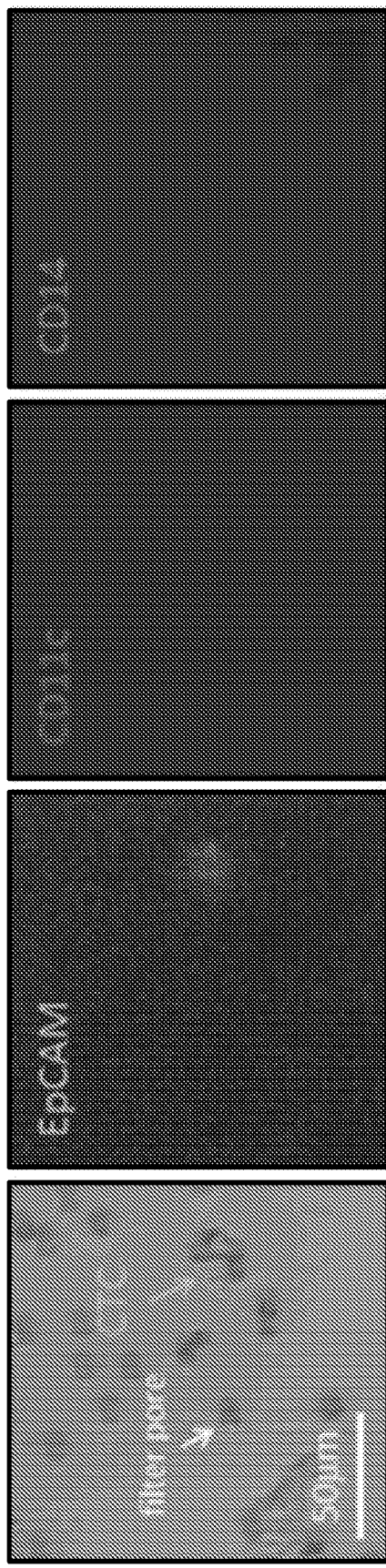
FIG. 3: Images of CTCs and macrophages in the blood of prostate xenograft mice for the indicated markers. In the bottom panel, CTCs are depicted to be in the vicinity of M1 and M2 macrophages.
Figure 3:
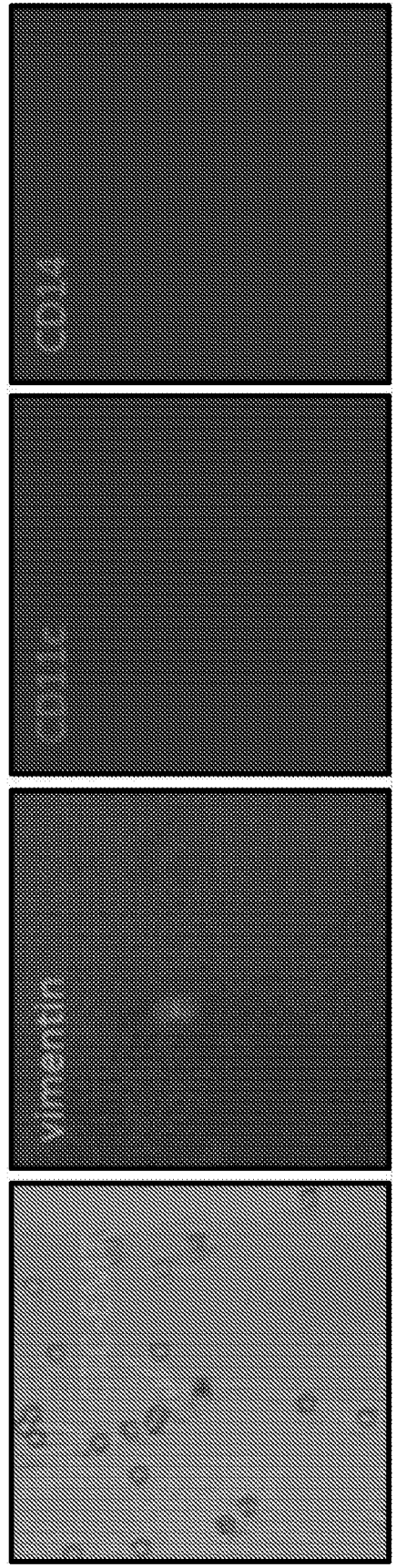
Figure 3:
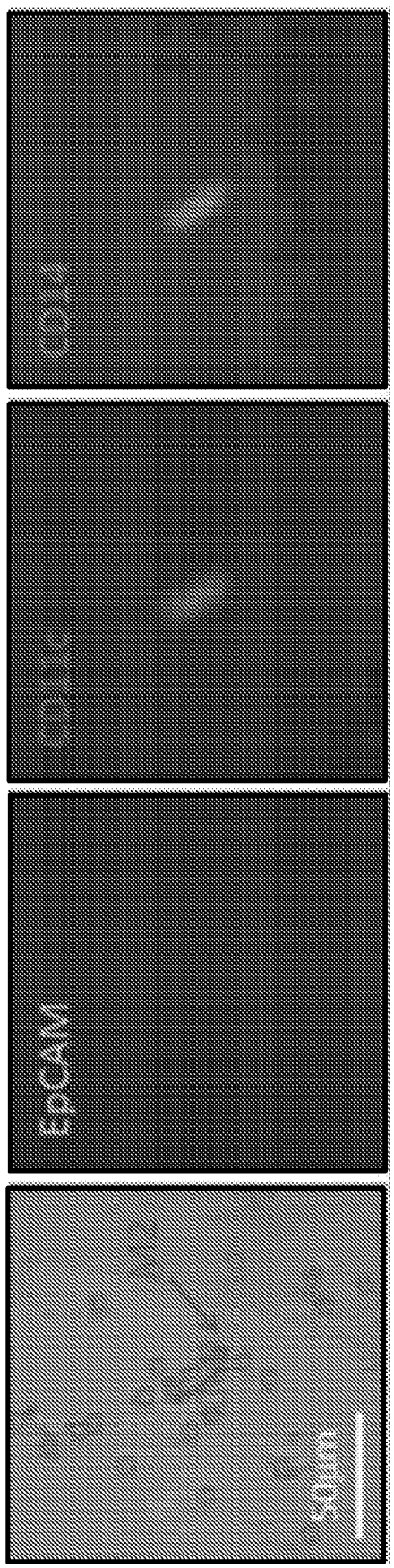
Figure 3:
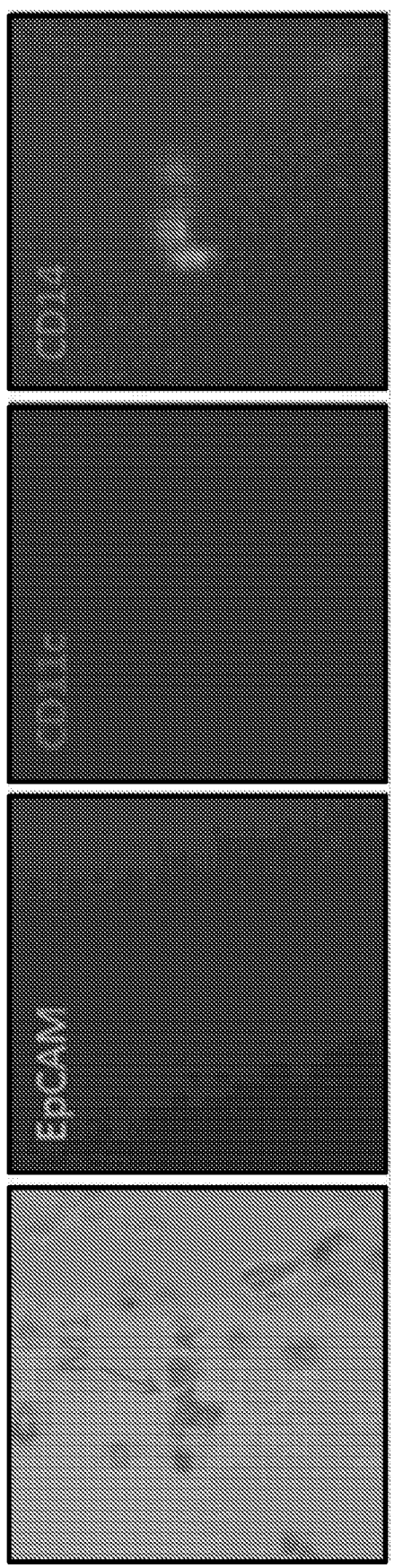
Figure 3:
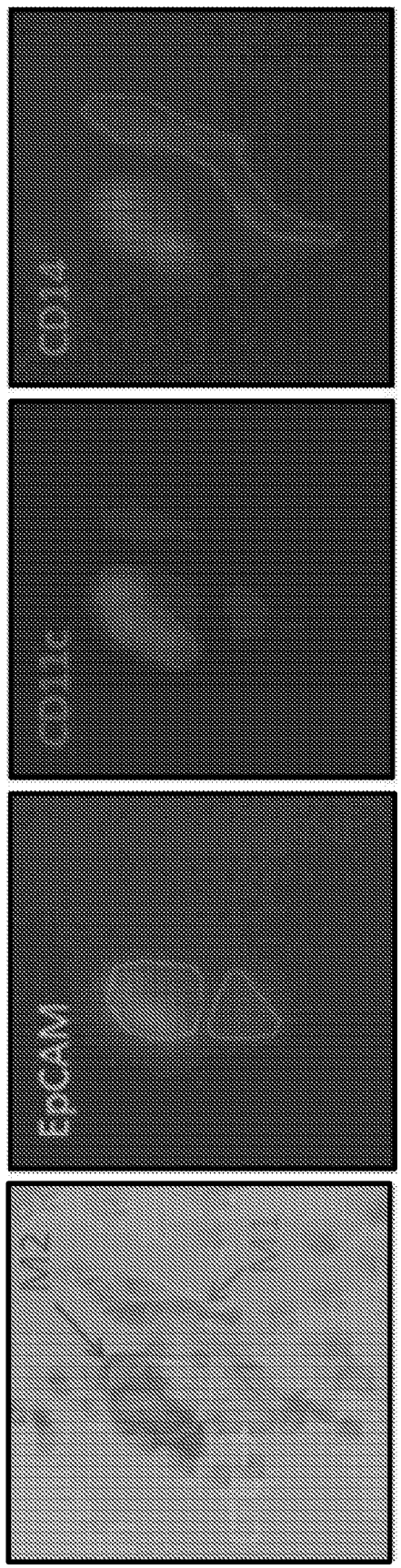
Figure 4:
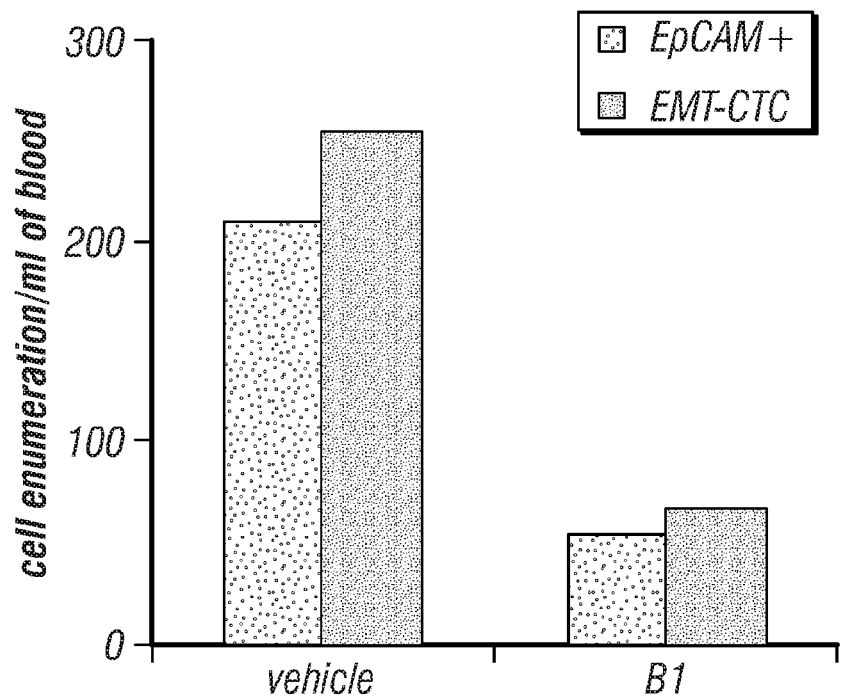
FIG. 4: Quantification of CTCs in mice treated with vehicle or B1 as measured by expression of EpCAM or vimentin.

Both CTCs and macrophages, as well as their pairs and clusters, were found to be abundant in the blood of both mice (FIG. 3). The B1-treated mouse had a significantly lower numbers of CTCs, correlating with the low burden of the primary tumor (FIG. 4).

Figure 5:
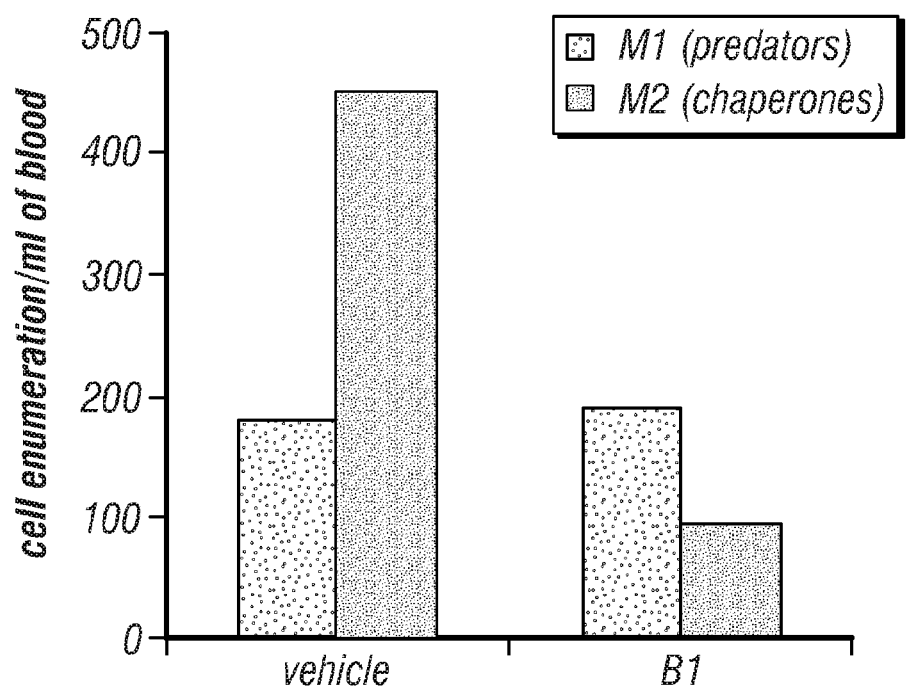
FIG. 5: Number of M1 predator (anti-tumor) macrophages and M2 (pro-tumor) macrophages in the blood of mice treated with vehicle or B1.

However, the numbers of circulating macrophages were also much lower in the blood of the B1-treated mouse. Interestingly, the number and types of macrophages differed grossly between vehicle treated and the B1-treated animal. As demonstrated in FIG. 5, the number of M1 predator (anti-tumor) macrophages was very similar in both mice; however, the control mouse had more than four-times more M2 pro-tumor macrophages as compared to the control mouse. Consistently, the ratios of pro-tumor and anti-tumor macrophages in control and B1-treated mouse were approximated as 2.5 and 0.5, respectively.

It was postulated that the differences in profiles of circulating macrophages, which may destroy CTCs or help them in seeding metastases, are indicative of the metastatic potential of CTCs. To determine the metastatic potential of CTCs isolated from the blood of human prostate cancer patients and mouse cancer models, biophysical profiling by atomic force microscopy (AFM) was employed. This method was used to confirm the decreased aggressiveness of CTCs isolated from the B1-treated mouse.

In short, to determine the mechanical phenotype of cells Peak Force Quantitative Nanomechanical Atomic Force Microscopy (PF QNM AFM) imaging was employed. The underlying principles of the method are presented in FIG. 6 and FIG. 7. AFM is a type of stylus profilometry. In this particular AFM technique, a micro-sized probe (tip) interacts with a cell surface with strictly controlled force. At each point of contact, the tip position and the "force plot" presenting mechanical interactions of the tip with a cell surface are recorded. Images are created during raster scanning by the tip. The parameters extracted from the force plots are assembled into topographical (cell morphology) and mechanical maps. The mechanical parameters include elasticity (i.e., pressure needed to indent the cell in a reversible manner), deformation (i.e., the depth of maximal indentation enforced by the probe without breaking the cell membrane), and adhesion (i.e., force needed to lift the tip from the cell surface during the probe withdrawal).

Figure 7:
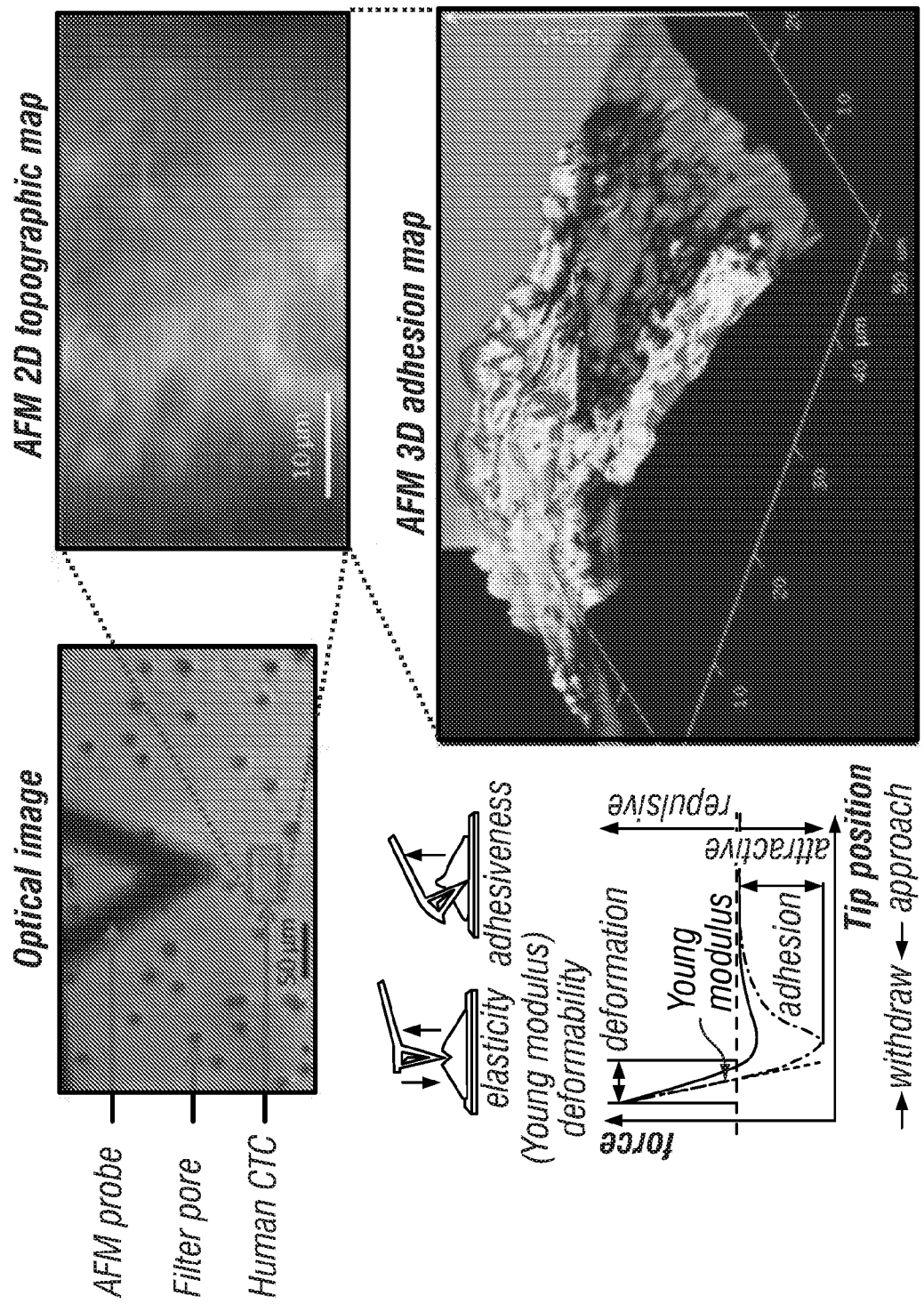
FIG. 7: Exemplary images acquired by PF QNM AFM useful for probing aggressiveness of CTCs. (Top left) Optical image showing a filter with a collected CTC. To the right is the 2 dimensional AFM topographic image of the same cell (Colors are artificial with darker colors corresponding to the lower object and the lighter color corresponding to taller objects). (Bottom right) Adhesion pseudo 3 dimensional image of the same cell. (Colors are artificial with the cooler color marking areas of lower adhesion and other colors marking high adhesion areas.)

A single AFM scan also provides a shape of the cell to distinguish between epithelial-like and mesenchymal-like phenotypes, and roughness of the cell surface that correlates with activity of apoptotic and EMT pathways (Chen et al, 2013; Osmulski et al., 2014). The integrated inverted fluorescent microscope allows collecting correlative immunocytochemical data about the scanned cells (FIG. 7).

Figure 6:
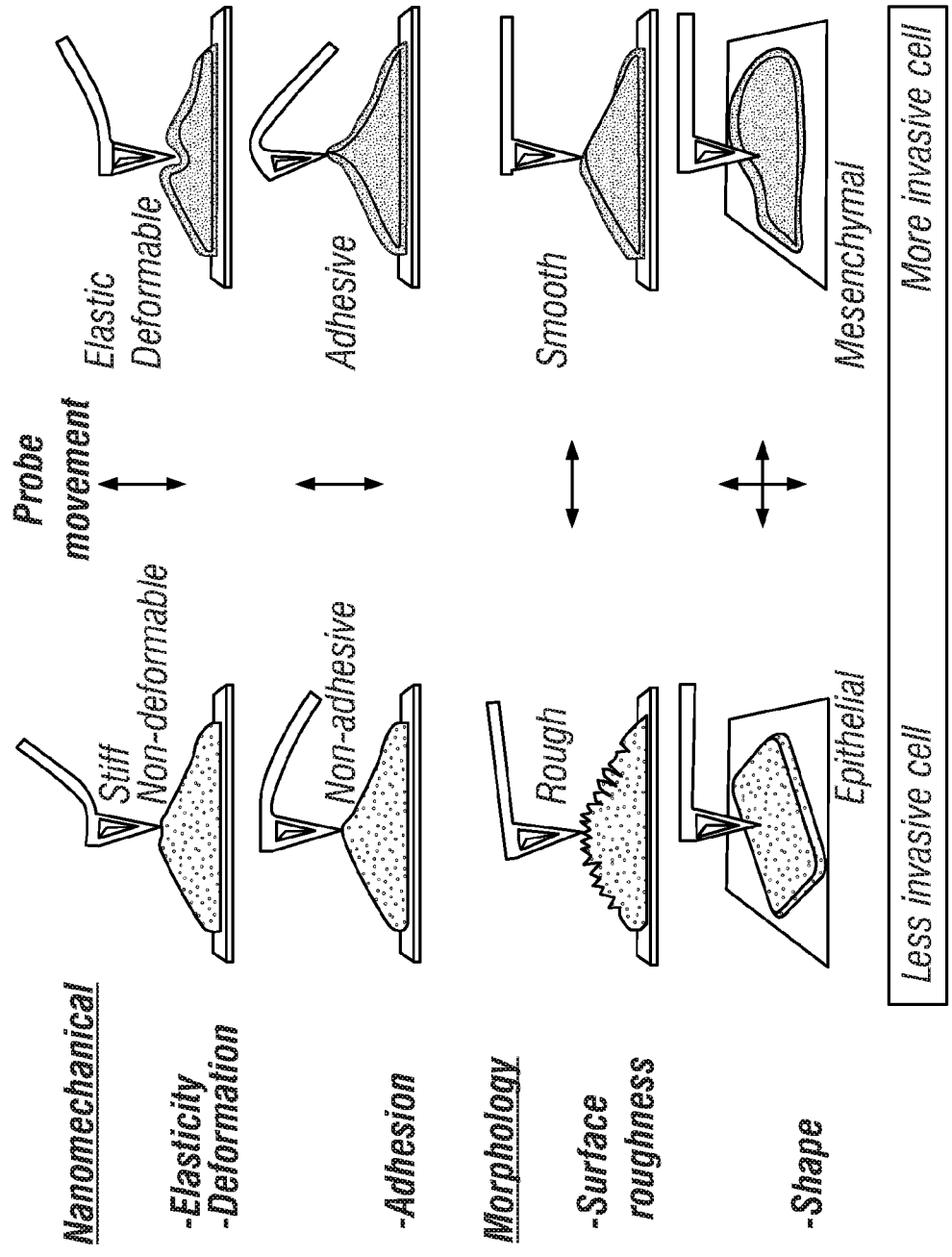
FIG. 6: Schematic depicting biophysical parameters acquired in Peak Force Quantitative Nanomechanical Atomic Force Microscopy (PF QNM AFM) scan of CTCs.

The biophysical parameters acquired in a single AFM scan of a CTC are presented in FIG. 6. The probe (tip on a cantilever) indents (vertical movement) and scans (lateral movement) the cell surface. After 10-15 min scan of a 1000-2000 μm² area, 5 maps of cell morphology, surface topography, elasticity, deformation, and adhesion (FIG. 6) are computed from the force plots (FIG. 7) created for each of the 4000-65,500 single tip-cell contact points with horizontal resolution of 100 nm, vertical resolution of 10 nm and forces as low as 100 pN. It is established that cancerous cell are much softer, deformable and more adhesive than their normal counterparts (Osmulski et al., 2014).

Figure 8:
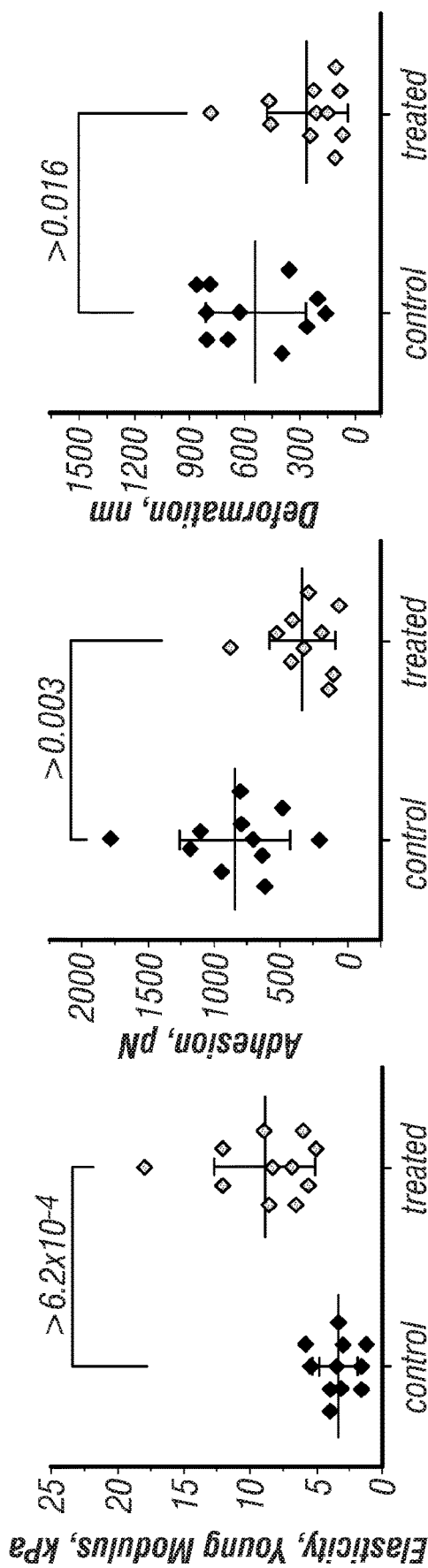
FIG. 8: Parameters of CTCs obtained from biophysical profiling including elasticity, adhesion, and deformation.

As demonstrated in FIG. 8, it was found by the biophysical profiling that CTCs isolated from the blood of B1-treated mouse had low aggressiveness: the cells were harder (i.e., higher Young modulus), less deformable, and less adhesive than CTCs from the vehicle treated mouse, an indication of the less aggressive disease consistent with the observed tumor shrinkage (FIG. 2). Thus, the studies suggest that B1 may be used to decrease the number of CTCs and associated macrophages for the prevention or treatment of cancer metastasis.

Example 2—B1 Maximum Tolerated Dose Study

Figure 9:
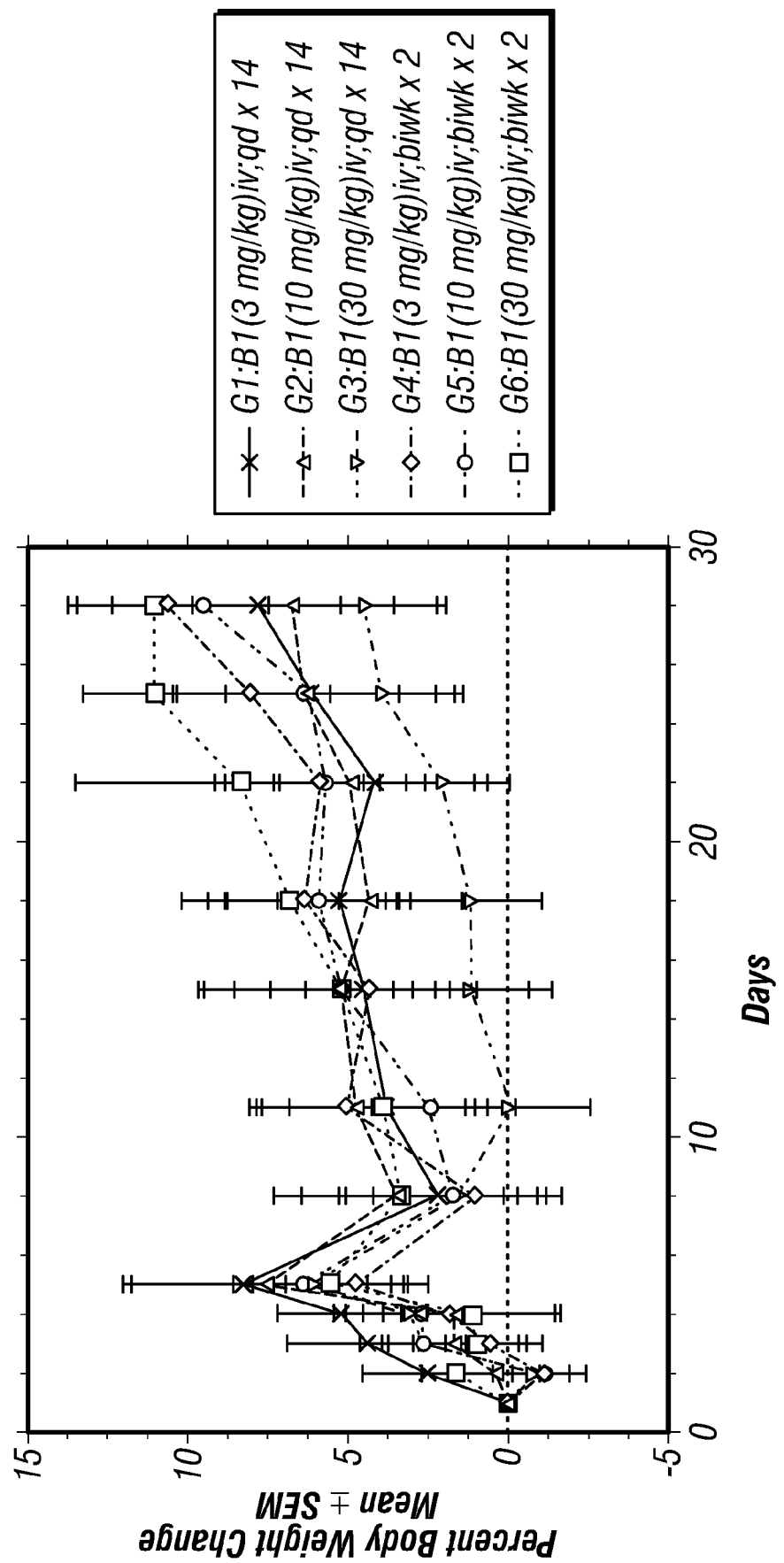
FIG. 9: Percent body weight change in mice treated with indicated concentration of B1 for dose study.

A study to determine the maximum tolerated dose was performed on 30 female CB. 17 SCID mice divided into six groups, five animals each. B1 was administered intravenously (i.v.) once a day (q.d.; three groups) or biweekly (three groups), at concentrations of 3 mg/kg, 10 mg/kg or 30 mg/kg, dissolved in 5% ethanol, 5% cremophor in water with 5% dextrose [D5W]. Mice were treated for 28 days, weighted daily on days 1-5 and then on a twice weekly schedule until day 28. They were observed frequently for adverse effects of treatment. None of the animals died during the duration of the experiment and no adverse effects on their behavior were observed. No statistically significant differences in body weight were detected between the groups (FIG. 9). Thus, B1 is non-toxic for mice even at the highest tested dose, 30 mg/kg.

The PD/PK study performed with mice xenografted with human multiple myeloma cells (RPMI 8226) revealed that a single 30 mg/kg dose of B1 administered intravenously (i.v.) localized to the xenografted tumor site. The study involved 11 female SCID mice, with 3 control mice injected with vehicle (5% ethanol, 5% cremophor in water with 5% dextrose [D5W]) and 9 mice injected with B1. The presence of B1 was detected by mass spectrometry in the tumors of B1-injected mice 8 and 12 hours post-injection, at concentrations up to 30.5 ng/g.

Example 3—B1 and Related Compounds Inhibit Cancer Metastasis

Figure 18:
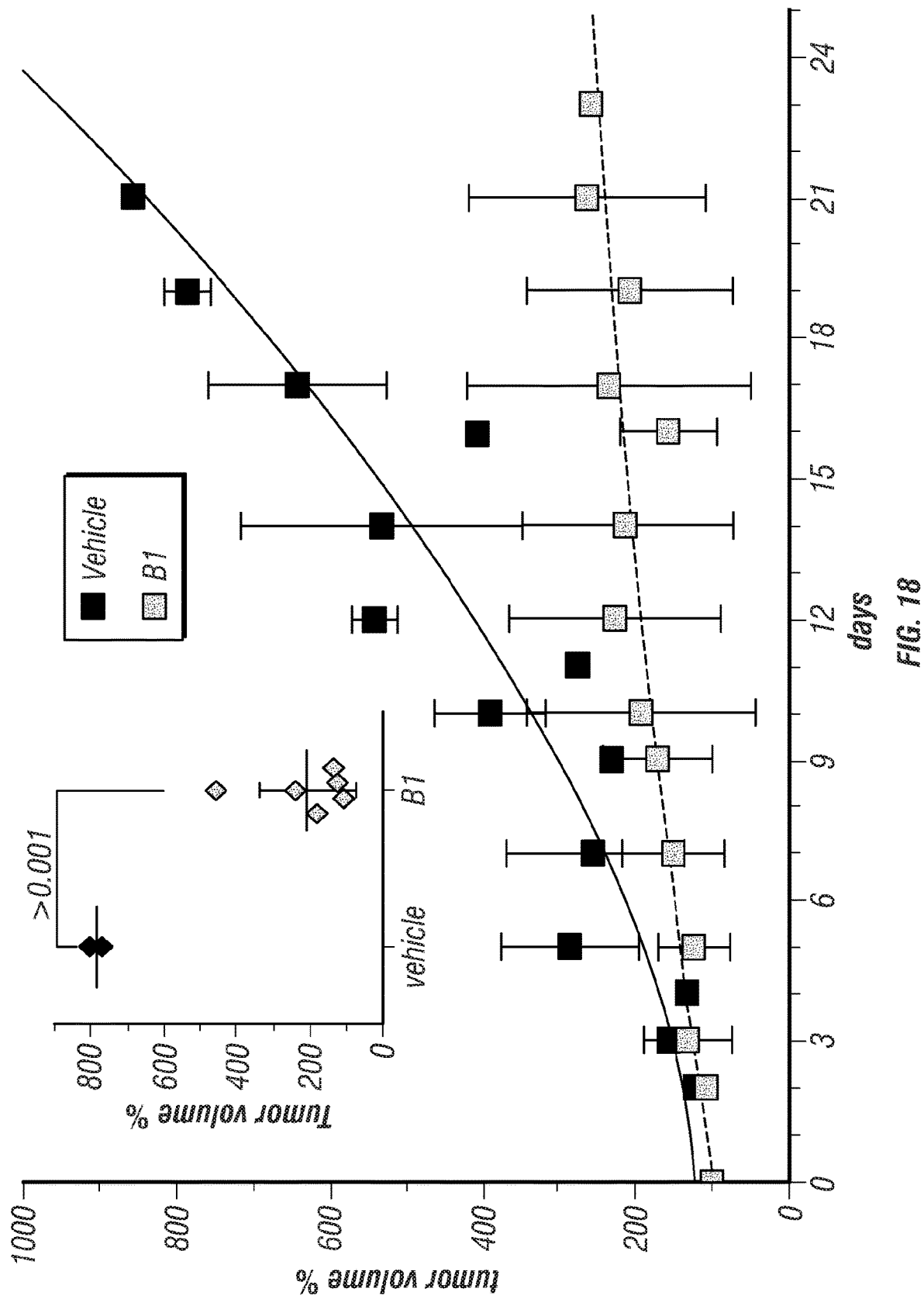
FIG. 18. Treatment with B1 significantly attenuates the growth of tumor in mouse xenograft prostate cancer model. The efficacy study was performed with mice xenografted with human cultured androgen-independent prostate cancer cells C4-2. The study involved eleven NOD-SCID mice. Eight tumor-growing mice were treated intra-tumorally (IT) with 30 mg/kg B1 twice a week for up to three weeks. The control group (four mice) received a B1 vehicle (dimethylsulfoxide; DMSO). Tumor sizes were measured twice a week. The tumor growth was significantly attenuated in the B1-treated group, as compared with the control group. B1 treatment did not result in detectable changes in the weight of animals (FIG. 9).

As shown herein, B1 exerts anti-metastatic actions with multiple mechanisms. First, the drug attenuates the growth of the primary tumor. Large tumors shed large number of metastasis seeding circulating tumor cells into circulation, thus increasing the chance of successful colonization of metastatic sites. Significant inhibition of tumor growth was achieved in pilot mouse studies with mice xenografted with human cultured androgen-independent prostate cancer cells C4-2 (FIG. 2 with a pair of nude mice; FIG. 18, with four control and eight B1-treated mice).

Figure 11:
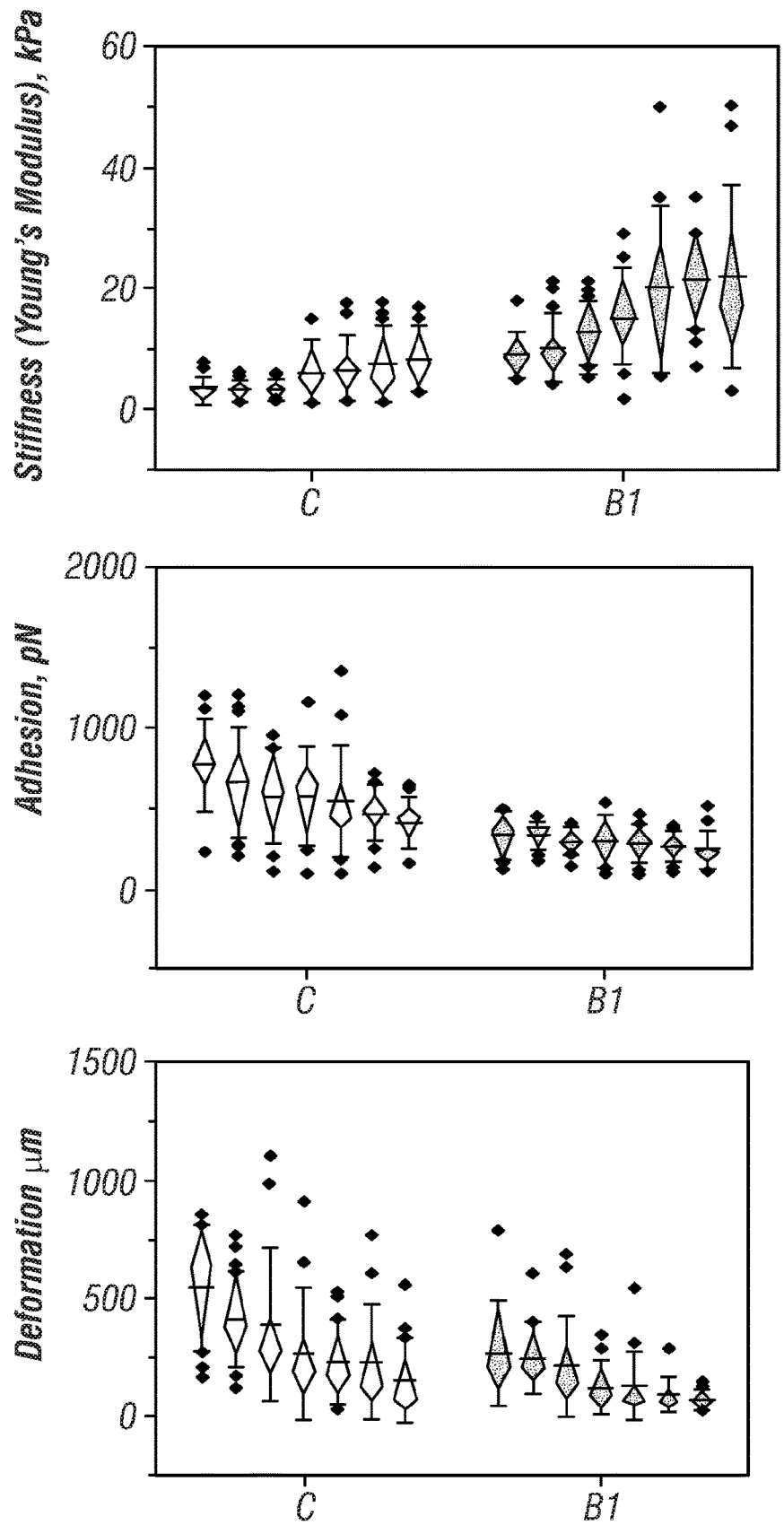
FIG. 11: Box plots of mechanical properties of CTCs measured with atomic force microscopy (AFM) show distinct distribution of properties for cells isolated from blood of control and B1 treated mice. In general, CTCs of the treated animals are stiffer (less elastic, larger Young's modulus), less adhesive and less deformable comparing to the control group. Such cells are less likely to successfully colonize distinct organs since they are too rigid for the hostile high pressure blood stream. Therefore, their low adhesiveness supporting long distance travel may be nullified by their low flexibility. Such a shift of the CTCs properties substantially limits capability of these cells to start metastasis. CTCs were disseminated from primary tumors induced in nude mice with C4-2 cells.
Figure 12:
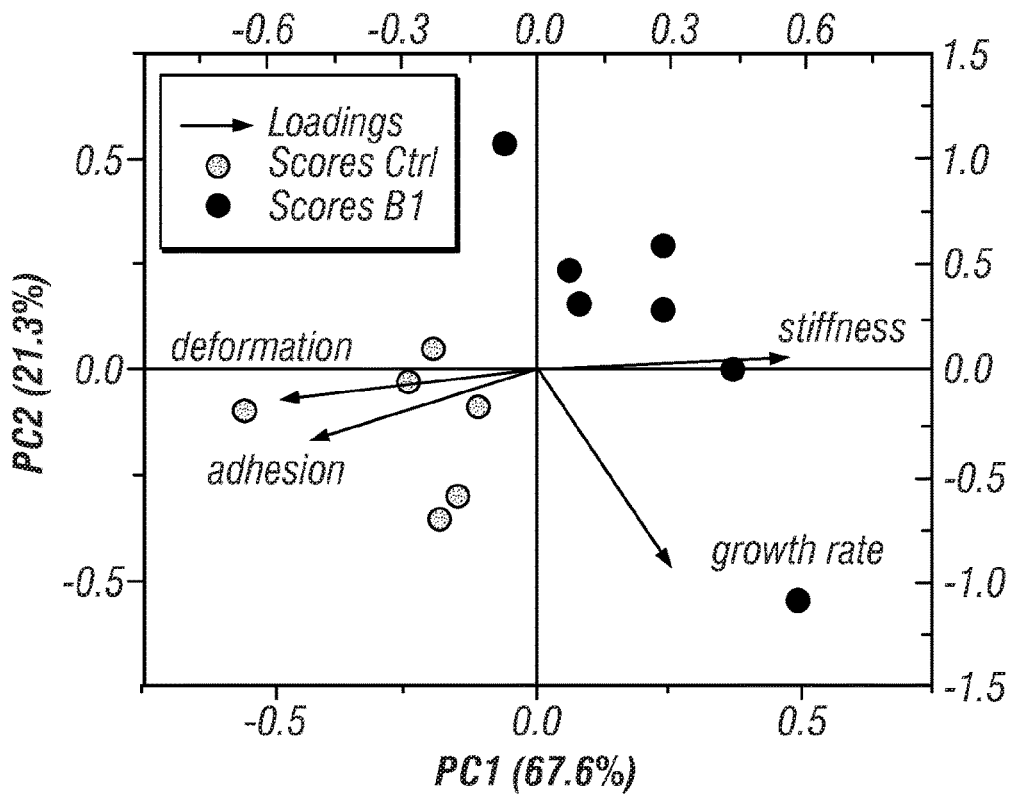
FIG. 12: Mechanical properties of mice CTCs were measured with AFM. Each data point represents an average calculated from at least 10 cells isolated from single mouse. The graph shows distinct association between deformation of cells and their stiffness (elasticity) for control and B1-treated mice. This finding suggests reorganization of cytoskeleton in CTCs isolated from blood of the B1-treated mice toward less invasive (harder and less deformable) phenotype.
Figure 13:
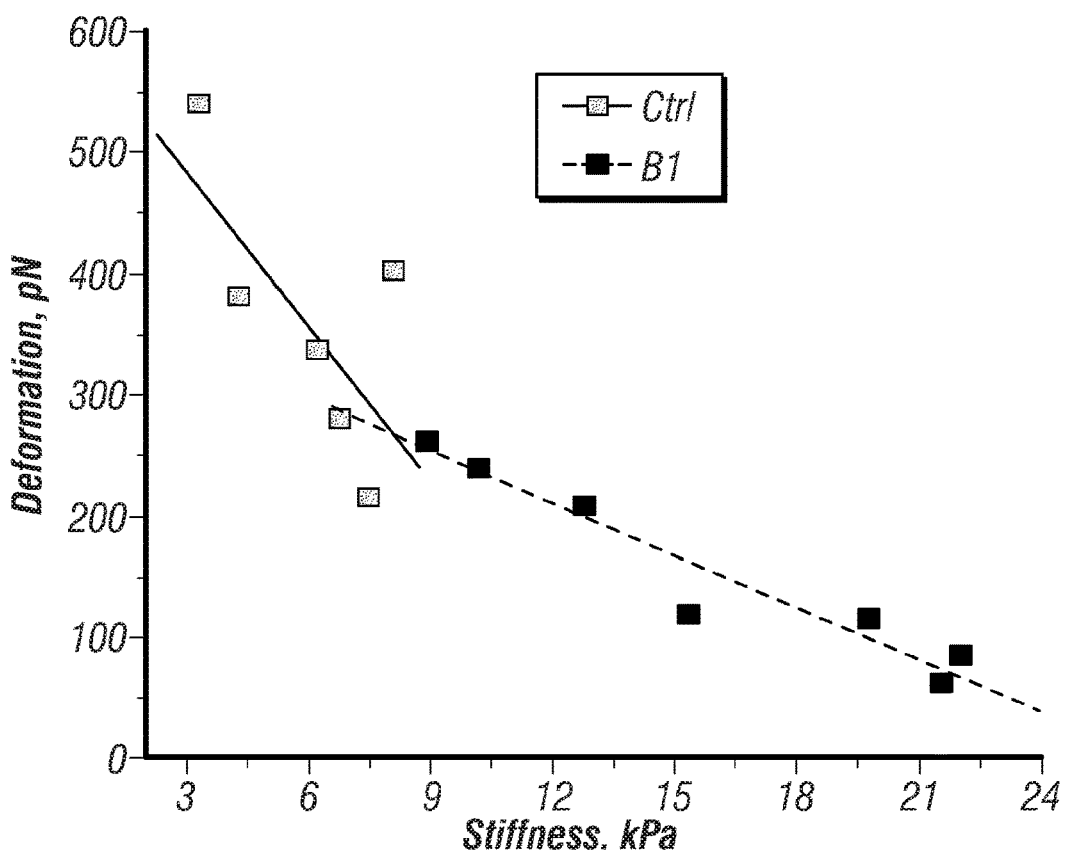
FIG. 13: Principal Component Analysis (PCA) performed on mechanical properties of CTCs as determined with AFM and tumor growth rate shows complete separation of the control and B1-treated cases. Dimensionality reduction indicates that the mice in these two groups differed in their stiffness and adhesion and these components explained almost 89% of samples variance. The plot implies that mechanical properties of CTCs isolated from the B1-treated mice are much less fitted toward metastatic invasion.
Figure 14:
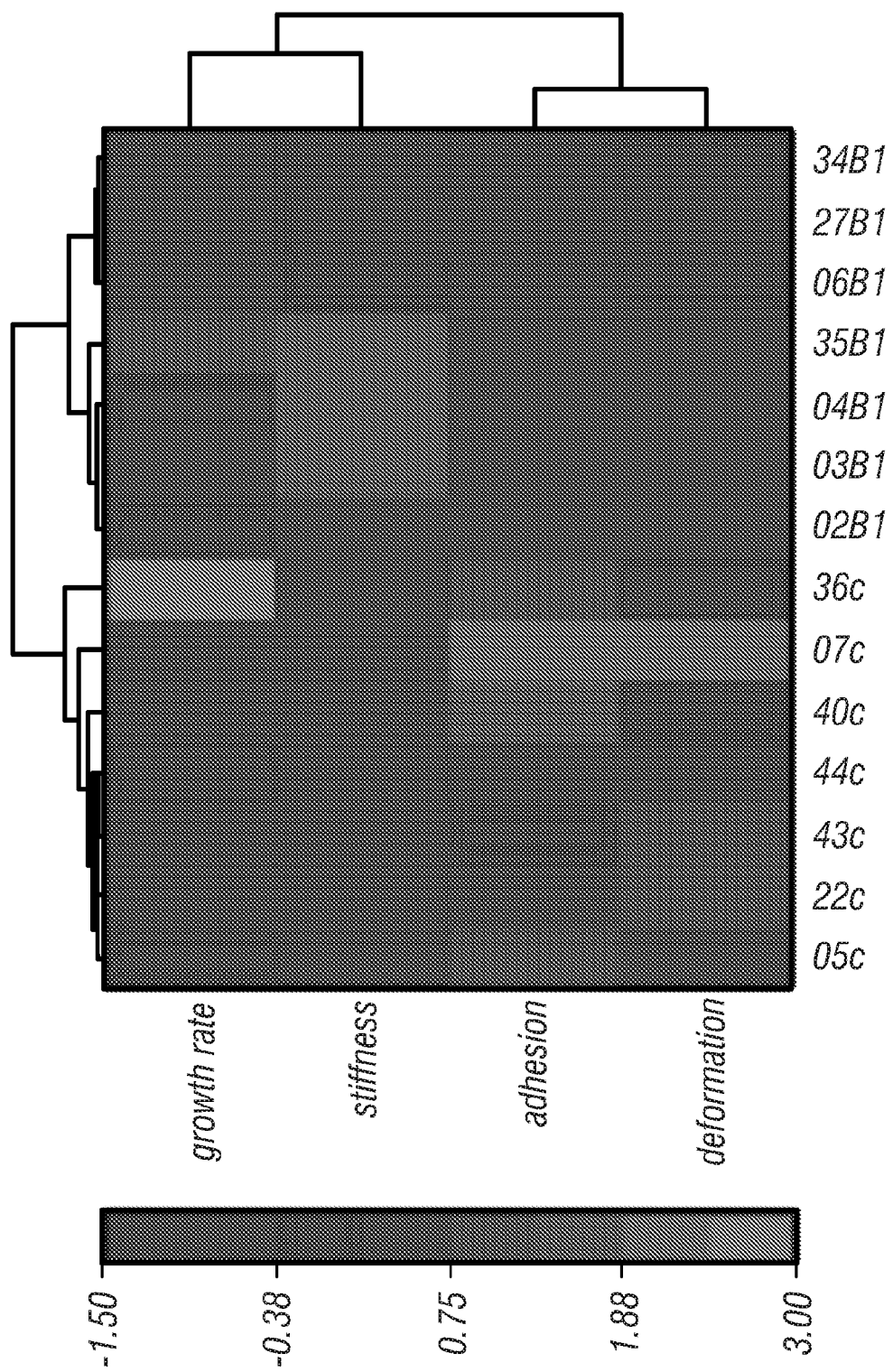
FIG. 14: A heat map resulting from cluster analysis of mechanical properties of CTCs as determined with AFM and tumor growth rates. Control animals (c) formed a separate cluster characterized by lower cell stiffness (they are more elastic), higher stickiness and larger deformability and slightly faster tumor growth than the B1-treated mice. The tumor growth rate and stiffness parameters clustered together, whereas adhesion (stickiness) and deformation formed a separate cluster following the decreasing trend from control to B1-treated animals.

Second, the drug decreases aggressiveness of CTCs. The decrease is apparent by comparison of mechanical phenotypes of CTCs isolated from mice xenografted with human cultured androgen-independent prostate cancer cells C4-2, and treated with vehicle or with B1 (30 mg/kg). The data are presented in FIGS. 11-16 and in Table 1 (FIG. 11 is an extended version of FIG. 8).

Third, the drug boosts natural anti-cancer immune response. It promotes anti-metastatic profile of macrophages co-purifying with CTCs in the nude mice xenografted with human cultured androgen-independent prostate cancer cells C4-2, and treated with vehicle or with B1 (30 mg/kg). The drug-treated mice had generally lower number of the pro-cancer M2-type macrophages ("chaperones" for CTCs) and larger number of the anti-cancer M1-type macrophages ("predating" on CTCs). The data are presented in FIG. 15 and in Table 1. Data from one control and one treated mouse are presented in FIG. 5, with data from seven control and six treated mice presented below.

Figure 17A:
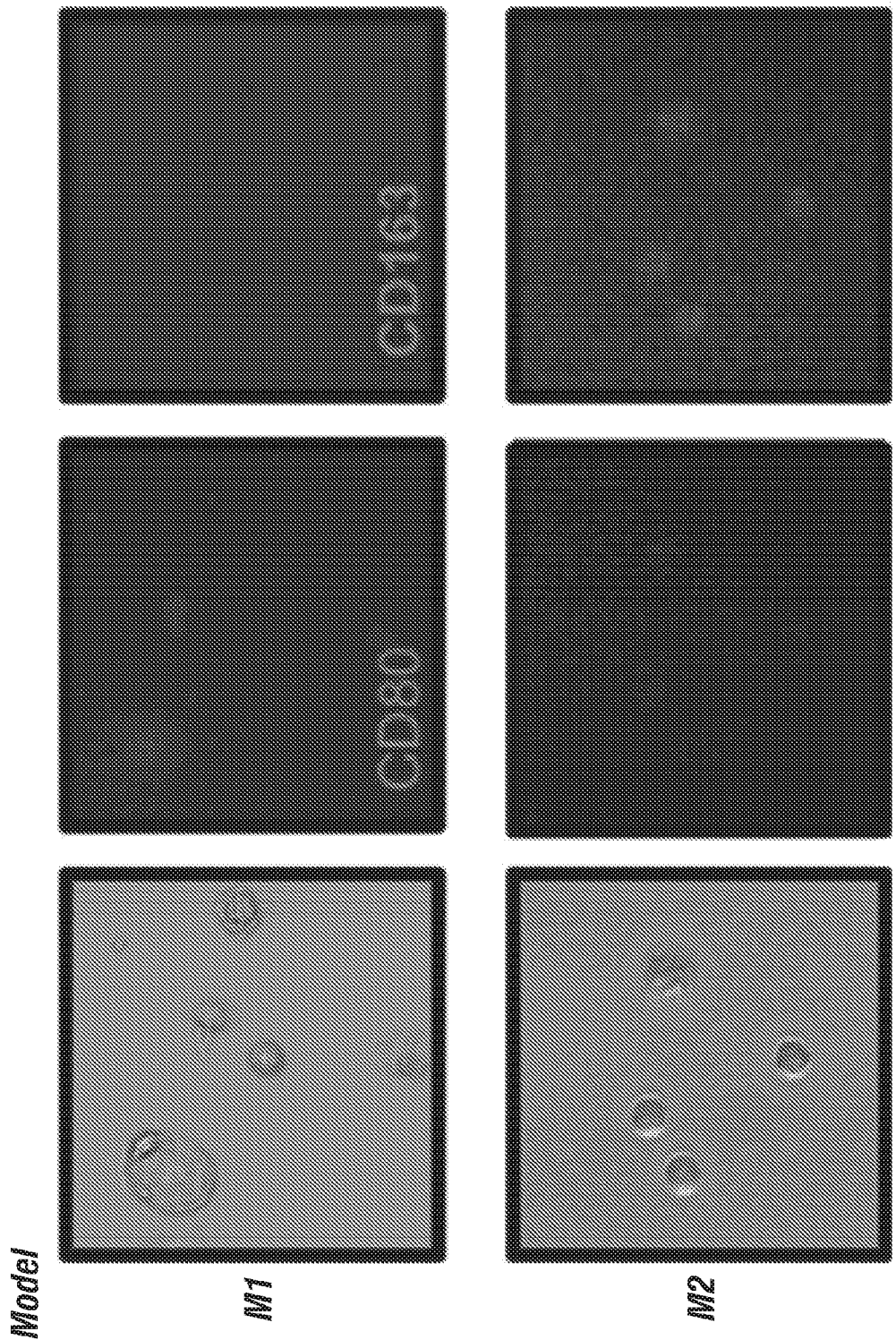
FIGS. 17A-B: Model M2-polarized macrophages are sensitive to the treatment with B1, in contrast to model M1-polarized macrophages.
Figure 17B:
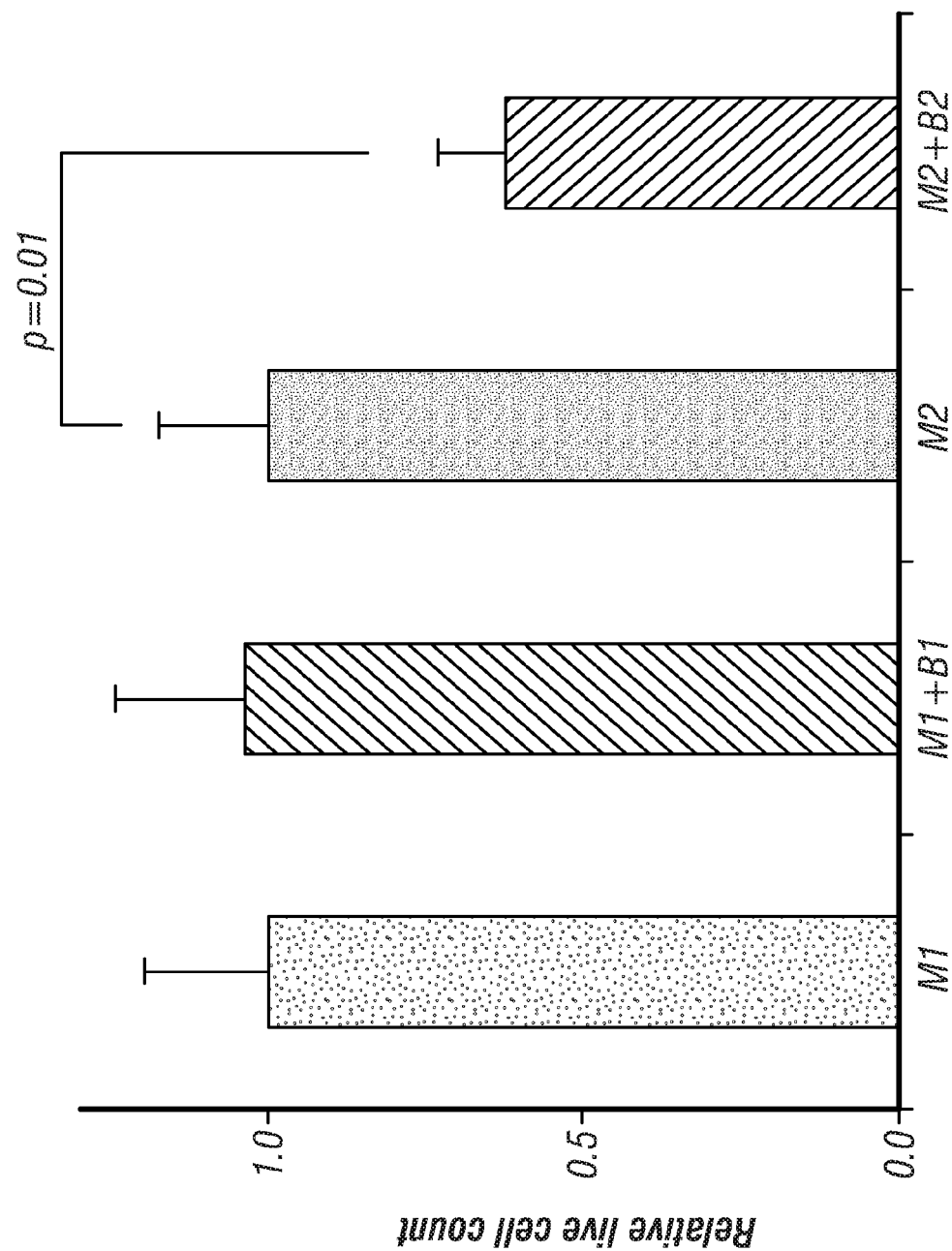

And fourth, the anti-M2 macrophages actions were confirmed in cell culture model. Apparently, treatment with B1 did not affect viability of M1-type macrophages, while significantly attenuating viability of M2-type macrophages. The data are presented in FIG. 17.

Figure 10:
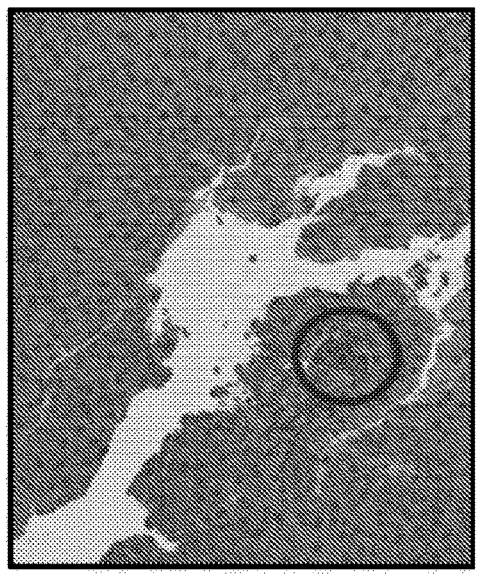
FIG. 10: H&E stained histological liver slices of control nude mice with a tumor induced using human C4-2 prostate cancer cells. Suspected micrometastasis sites are marked with black rings. A scale bar represents 500 µm. Micrometastasis was detected with an average frequency in the control group (untreated) 3.75 per mice, whereas in the B1 treated group it was 1.33 per mice.
Figure 10:
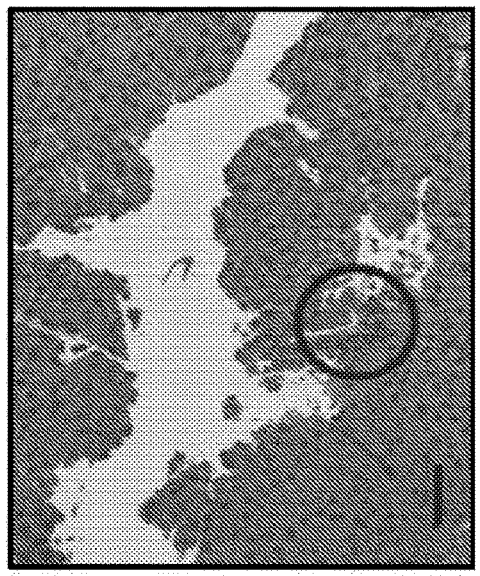
Figure 10:
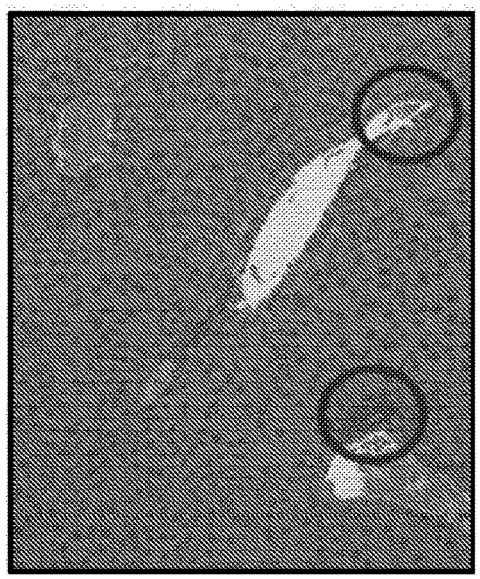

Importantly, in the second, third and fourth mechanisms, the drug acts independently from the size of primary tumor. This was an unexpected effect. The inventors demonstrated this independence by analyzing a selected group of seven control and six B1-treated mice characterized by similar rates of the growth of xenografted tumors. In these mice the tumor volumes increased generally 3× to 5×, with no significant difference between the control and B1-treated tumors. Still, the inventors observed the significantly lowered aggressiveness of CTCs and the anti-tumor profiles of circulating macrophages in the B1-treated mice. As a direct evidence of anti-metastatic actions, a decreased incidence of micrometastases in livers of B1-treated mice, as compared with the controls, was observed (FIG. 10).

In conclusion, the data presented here support the following beneficial effects of B1 and related compounds. First, when the primary tumor is surgically removed, treatment with B1 eliminates CTCs originating from remaining traces of tumor tissue without the need of toxic therapies aimed at killing the remaining tumor cells. Such therapies most often result in developing drug resistance and are always associated with serious side effects. Second, boosting the natural anti-cancer immune response of the patient with B1 treatment is a highly desired outcome. The effect will allow limiting the use of conventional anti-cancer therapeutics that kill cancer cells but also compromise the immune system of the patient. And third, combinations of B1 and low doses of conventional cytotoxic drugs will allow efficient eradication of cancer cells with minimizing harmful side effects to the patient.

TABLE 1

|  | PCA1 | PCA2 |
| --- | --- | --- |
| EpCAM | *0.4021* | 0.2200 |
| EMT | *0.4289* | 0.1465 |
| CTC clusters | *0.3283* | 0.0572 |
| M1 | 0.1357 | *0.3983* |
| M2 | *0.4358* | 0.1074 |
| CTC-M1 | 0.0355 | *0.3846* |
| CTC-M2 | 0.2516 | −0.3557 |
| Stiffness | −0.1958 | *0.4414* |
| Adhesion | 0.3082 | −0.2846 |
| Deformation | 0.2217 | −0.3966 |
| Growth rate | 0.3022 | 0.2217 |

Figure 15:
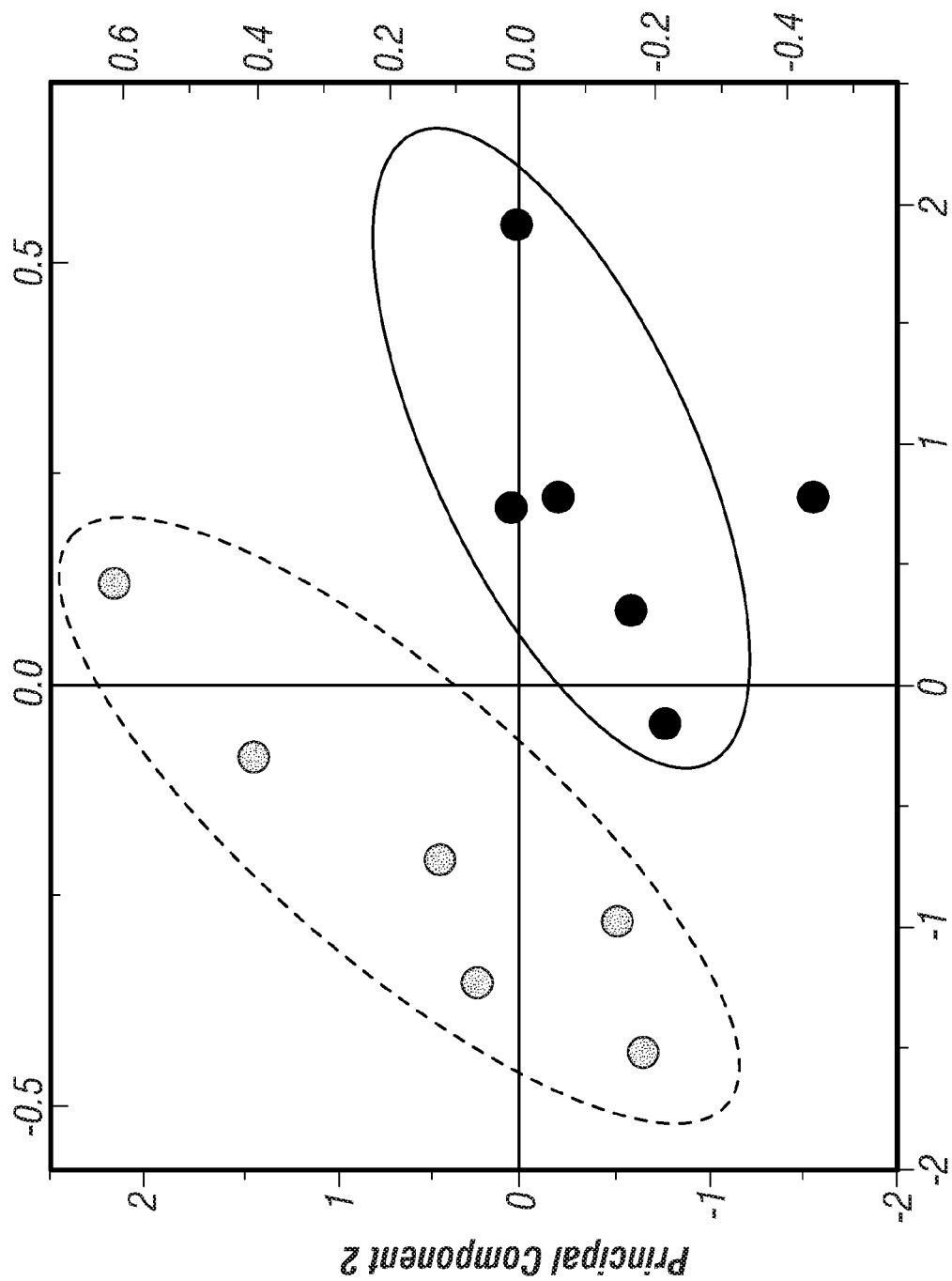
FIG. 15: PCA carried out on enumeration of CTCs, macrophages, their clusters and CTC mechanical properties shows that control and B1 treated mice form totally distinct groups. Each data point corresponds to data from a single mouse (right-most circle=ctrl, leftmost circle=B1). Ellipses show boundary of the 95% confidence.
Figure 16:
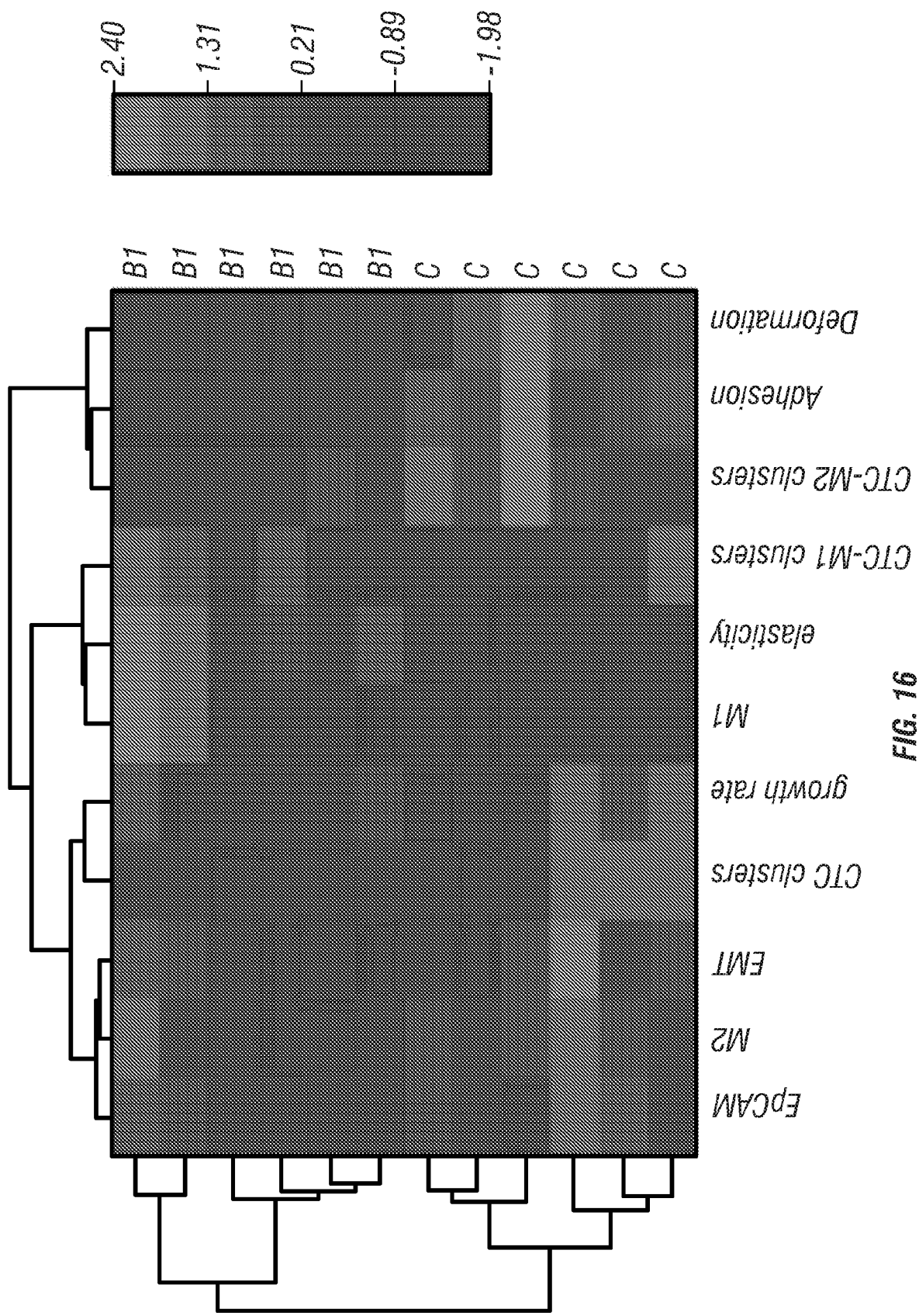
FIG. 16: Heat Map with cluster analysis performed on enumeration of CTCs, macrophages, their clusters and mechanical properties of CTCs shows that B1 treated mice have an advantage in suppressing metastasis. Clustering in both directions was executed with the Ward method using Euclidean distance. The two groups of animal represented in the rows formed two clearly separated classes. Clustering of the enumeration and mechanical parameters suggests important molecular and physiological relationships such as: (1) limited formation of CTC-M2 (chaperoning) clusters when CTCs become less sticky and deformable after B1 treatment; (2) enhanced formation of M1-CTC (predatory) clusters with less elastic CTCs after B1 treatment, (3) diminished formation of CTCs clusters that enhance survival of CTCs in a blood stream and increase probability to start metastasis in B1 treated mice, (4) number of highly invasive post-EMT CTCs was also diminished in the treated group of mice.

PCA generated loads for two components (PCA1 and PCA2; FIG. 15) demonstrate that the major principal components that influence classification of the animals into two groups are for PCA1 metastasis promoting (marked in italics): enumeration of EpCAM positive cells, CTCs undergoing EMT, CTC clusters and M2 (chaperoning) macrophages, and for PCA2 metastasis limiting enumeration of M1 (predatory) macrophages, their clusters with CTCs and high CTCs stiffness. At the same time, the tumor growth rate displayed similar loading for both components.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Austin-Ward and Villaseca, *Revista Medica de Chile*, 126 (7):838-845, 1998.
Bukowski et al., *Clinical Cancer Res.*, 4(10):2337-2347, 1998.
Camacho et al. *J Clin Oncology* 22(145): Abstract No. 2505 (antibody CP-675206), 2004.
Chen et al., *Prostate* 73, 813-826, 2013.
Christodoulides et al., *Microbiology*, 144(Pt 11):3027-3037, 1998.
Davidson et al., *J. Immunother.*, 21(5):389-398, 1998.
*Handbook of Pharmaceutical Salts: Properties, and Use*, Stahl and Wermuth Eds.), Verlag Helvetica Chimica Acta, 2002.
Hanibuchi et al., *Int. J. Cancer*, 78(4):480-485, 1998.
Hellstrand et al., *Acta Oncologica*, 37(4):347-353, 1998.
Hollander, *Front. Immun.*, 3:3, 2012.
Huang et al., *Oncotarget*, 7(47), 77124-77137, 2016.
Hui and Hashimoto, *Infection Immun.*, 66(11):5329-5336, 1998.
Hurwitz et al. *Proc Natl Acad Sci USA* 95(17): 10067-10071, 1998.
International Patent Publication No. WO 00/37504
International Patent Publication No. WO 01/14424
International Patent Publication No. WO 01/14424
International Patent Publication No. WO 98/42752
International Patent Publication No. WO1995001994
International Patent Publication No. WO1998042752
International Patent Publication No. WO2000037504
International Patent Publication No. WO2001014424
International Patent Publication No. WO2006/121168
International Patent Publication No. WO2009/101611
International Patent Publication No. WO2009/114335
International Patent Publication No. WO2010/027827
International Patent Publication No. WO2011/066342
International Patent Publication No. WO2015016718
Lander, et al., *Nature*, 482:186-191, 2012.
Liu, et al., *Molecular Cell*, 24:39-50, 2006.
*March's Advanced Organic Chemistry: Reactions, Mechanisms, and Structure*, 2007.
Massague et al., *Nature* 529:21, 298-306, 2016.
Mokyr et al., *Cancer Res* 58:5301-5304, 1998.
Osmulski et al., *Prostate* 74, 1297-1307, 2014.
Pardoll, *Nat Rev Cancer*, 12(4): 252-64, 2012.
Qin et al., *Proc. Natl. Acad. Sci. USA*, 95(24):14411-14416, 1998.
U.S. Pat. No. 4,870,287
U.S. Pat. No. 5,739,169

U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 6,207,156
U.S. Pat. No. 8,017,114
U.S. Pat. No. 8,119,129
U.S. Pat. No. 8,329,867
U.S. Pat. No. 8,354,509
U.S. Pat. No. 8,735,553
U.S. Patent Publication No. US20110008369
U.S. Patent Publication No. US2014/0154689
U.S. Patent Publication No. US2014022021
U.S. Patent Publication No. US20140294898
U.S. Patent Publication No. US2016/0152567
Wynn et al., Nature, 496, 445-454, 2013.

What is claimed is:

1. A method of treating cancer metastasis in a subject comprising administering to the subject an effective amount of (3-(3,4,5-trimethoxyphenyl)propyl 1-(2-cyclohexyl-2-oxoacetyl)piperidine-2-carboxylate (B1), wherein administering B1 results in a decreased ratio of M2 macrophages to M1 macrophages in said subject wherein the cancer is selected from lung, breast, ovary, head and neck, liver, pancreas, or prostate cancer.

2. The method of claim 1, wherein the ratio of M2 macrophages to M1 macrophages is decreased at least 2-fold as compared to the ratio prior to administering B1.

3. The method of claim 1, wherein the ratio of M2 macrophages to M1 macrophages is decreased at least 4-fold as compared to the ratio prior to administering B1.

4. The method of claim 1, wherein the ratio of M2 macrophages to M1 macrophages is measured from pre-treatment and post-treatment blood samples obtained from said subject.

5. The method of claim 1, wherein said subject has been determined to have a M2 macrophage to M1 macrophage ratio greater than 1 prior to administering B 1.

6. The method of claim 1, wherein said subject has been determined to have a M2 macrophage to M1 macrophage ratio greater than 2 prior to administering B 1.

7. The method of claim 1, wherein treating cancer metastasis is further defined as reducing the metastatic potential of a cancer by interfering with the interaction of circulating tumor cells (CTCs) and tumor-associated macrophages (TAMs) in said subject.

8. The method of claim 1, wherein treating cancer metastasis results in decreased CTCs and TAMs, and/or decreased CTC aggressiveness.

9. The method of claim 4, wherein said subject has been determined to have an increased number of CTCs and/or TAMs in the pre-treatment sample as compared to a control level.

10. The method of claim 7, wherein the CTCs express EpCAM and/or an EMT marker.

11. The method of claim 10, wherein the EMT marker is selected from the group consisting of vimentin, N-cadherin, FSP1, β-catenin, Snail, Slug, ZEB1, and α-SMA.

12. The method of claim 1, wherein the prostate cancer is androgen-independent prostate cancer.

13. The method of claim 1, wherein B1 is administered to the patient once.

14. The method of claim 1, wherein B 1 is administered to the patient two or more times.

15. The method of claim 1, wherein B1 is administered intravenously.

16. The method of claim 1, wherein the method further comprises a second therapy.

17. The method of claim 16, wherein the second therapy is one or more therapeutic agents, a surgery, a radiotherapy, or an immunotherapy.

18. The method of claim 16, wherein the second therapy is a chemotherapeutic agent.

19. The method of claim 18, wherein the chemotherapeutic agent is a proteasome inhibitor.

20. The method of claim 1, wherein treating results in the activity of M2 macrophages in said subject being reduced, and/or the activity of M1 macrophages in said subject not being affected, and/or the size or growth rate of a primary tumor not being affected.

21. A method of evaluating the efficacy of (3-(3,4,5-trimethoxyphenyl)propyl 1-(2-cyclohexyl-2-oxoacetyl)piperidine-2-carboxylate (B1) in reducing metastatic potential of a cancer cell comprising determining the ratio of M2 macrophages to M1 macrophages in a post-treatment sample.

22. The method of claim 19, wherein the proteasome inhibitor is selected from bortezomib, carfilzomib, ixazomib, delanzomib, oprozomib, or marizomib.

* * * * *